(12) United States Patent
Bellaire et al.

(10) Patent No.: US 8,449,916 B1
(45) Date of Patent: May 28, 2013

(54) ANTIMICROBIAL COMPOSITIONS AND METHODS

(75) Inventors: Bryan Bellaire, Ankeny, IA (US); Balaji Narasimhan, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 156 days.

(21) Appl. No.: 12/940,872

(22) Filed: Nov. 5, 2010

Related U.S. Application Data

(60) Provisional application No. 61/259,061, filed on Nov. 6, 2009.

(51) Int. Cl.
*A61K 9/14* (2006.01)
*A61K 9/51* (2006.01)
*C08G 67/04* (2006.01)
*C08L 73/02* (2006.01)
*C09D 173/02* (2006.01)

(52) U.S. Cl.
CPC .............. *A61K 9/14* (2013.01); *A61K 9/5146* (2013.01); *C08G 67/04* (2013.01); *C08J 2373/02* (2013.01); *C08L 73/02* (2013.01); *C09D 173/02* (2013.01); *Y10S 977/906* (2013.01)
USPC .......................................... 424/489; 977/906

(58) Field of Classification Search
None
See application file for complete search history.

(56) References Cited

U.S. PATENT DOCUMENTS

| | | | | |
|---|---|---|---|---|
| 4,857,311 | A * | 8/1989 | Domb et al. | 514/772.3 |
| 6,399,102 | B1 * | 6/2002 | Edwards et al. | 424/489 |
| 7,858,093 | B1 * | 12/2010 | Kipper et al. | 424/184.1 |
| 2007/0238173 | A1 * | 10/2007 | Yamagami et al. | 435/371 |

OTHER PUBLICATIONS

MP Torres, AS Determan, GL Anderson, SK Mallapragada, B Narasimhan. "Amphiphilic polyanhydrides for protein stabilization and release." Biomaterials, vol. 28, 2007, pp. 108-116.*
WC Lee, IM Chu. "Preparation and Degradation Behavior of Polyanhydrides Nanoparticles." Journal of Biomedical Materials Research Part B: Applied Biomaterials, vol. 84B, 2008, pp. 138-146, published May 1, 2007.*
KN Agwuh, A MacGowan. "Pharmacokinetics and pharmacodynamics of the tetracyclines including glycylcyclines." Journal of Antimicrobial Chemotherapy, vol. 58, 2006, pp. 256-265.*
Determan et al., "Encapsulation, stabilization, and release of BSA-FITC from polyanhydride microspheres", Journal of Controlled Release 100(1), 2004, pp. 97-109.
Kipper et al., "Design of an injectable system based on bioerodible polyanhydride microspheres for sustained drug delivery", Biomaterials. 23(22), 2002, pp. 4405-4412.
Shen et al., "Mechanistic relationships between polymer microstructure and drug release kinetics in bioerodible polyanhydrides", Journal of Controlled Release 82(1), 2002, pp. 115-125.
Jain et al., "Role of polyanhydrides as localized drug carriers", Journal of Controlled Release 103(3), 2005, pp. 541-563.
Determan et al., "The role of microsphere fabrication methods on the stability and release kinetics of ovalbumin encapsulated in polyanhydride microspheres" Journal of Microencapsulation 23(8), Dec. 2006, pp. 832-843.
Pfeifer et al., "Poly(ester-anhydride):poly(beta-amino ester) microspheres and nanospheres: DNA encapsulation and cellular transfection", International Journal of Pharmaceutics 304(1-2), 2005, pp. 210-219.
Shelke et al., "Synthesis and characterization of novel poly(sebacic anhydride-co-Pluronic F68/F127) biopolymeric microspheres for the con trolled release of nifedipine", International Journal of Pharmaceutics 345(1-2), 2007, pp. 51-58.
Hsu et al., "Local delivery of interleukin-2 and adriamycin is synergistic in the treatment of experimental malignant glioma", Journal of Neuro-Oncology 74(2), 2005, pp. 135-140.
Kipper et al., "Single dose vaccine based on biodegradable polyanhydride microspheres can modulate immune response mechanism", J. Biomed. Materi. Res. Part A. 76(4), 2006, pp. 798-810.
Berkland et al., "Microsphere size, precipitation kinetics and drug distribution control drug release from biodegradable polyanhydride microspheres", J. Control. Release. 94(1), 2004, pp. 129-141.
Fuller et al., "Intracellular delivery of core-shell fluorescent silica nanoparticles", Biomaterials 29(10), 2008, pp. 1526-1532.
Stokes et al., "The receptor-mediated uptake, survival, replication, and drug sensitivity of *Mycobacterium tuberculosis* within the macrophage-like cell line THP-I: a comparison with human monocyte-derived macrophages", Cellular Immunology 197(1), 1999, pp. 1-9.

(Continued)

*Primary Examiner* — Frederick Krass
*Assistant Examiner* — Isaac Shomer
(74) *Attorney, Agent, or Firm* — Billion & Armitage; Michael H. Haukaas

(57) ABSTRACT

The invention provides compositions and methods to treat microbial infections in animals, to inhibit the replication of microbes in infected cells, and to kill pathogens in infected cells. The methods can include administering to an animal in need of such treatment an effective antimicrobial amount of a composition comprising polyanhydride microparticles or nanoparticles that encapsulate a plurality of antimicrobial agents. The polyanhydride microparticles or nanoparticles can be, for example, copolymers of sebacic anhydride (SA) and 1,6-bis-(p-carboxyphenoxy)hexane (CPH) anhydride, copolymers of 1,8-bis(carboxyphenoxy)-3,6-dioxaoctane (CPTEG) anhydrides and 1,6-bis-(p-carboxyphenoxy)hexane (CPH) anhydride, or various combinations thereof. The microparticles or nanoparticles can accumulate in infected monocytes, dendritic cells, both, or on or in other infected cells, and degrade by surface erosion over a period of time to release the antimicrobial agents, thereby killing or inhibiting the microbes and treating the infection.

20 Claims, 16 Drawing Sheets

OTHER PUBLICATIONS

Bellaire et al., "Opsonized virulent *Brucella abortus* replicates within nonacidic, endoplasmic reticulum-negative, LAMP-1 positive phagosomes in human monocytes", Infection and Immunity 73(6), Jun. 2005, pp. 3702-3713.

Lecaroz et al., "Poly(D,L-lactide-coglycolide) particles containing gentamicin: pharmacokinetics and pharmacodynamics in *Brucella melitensis*-infected mice", Antimicrob. Agents Chemother, vol. 51 No. 4, Apr. 2007, pp. 1185-1190.

Ulery et al., "Polymer Chemistry Influences Monocytic Uptake of Polyanhydride Nanospheres", Pharmaceutical Research, vol. 26, No. 3, Mar. 2009, pp. 683-690.

* cited by examiner

**Enhanced Killing of Intracellular *B. abortus***

*Figure 13*

Continued Antibiotic Release by Serial Disk Transfer
Antimicrobial zone of inhibition generated on confluent
*Brucella canis* on solid media NZ = No Zone of Inhibition detected

A) Intracellular Bacterial Viability

B) Extracellular Bacterial Killing

ANTIMICROBIAL COMPOSITIONS AND METHODS

RELATED APPLICATIONS

This application claims priority under 35 U.S.C. §119(e) to U.S. Provisional Patent Application No. 61/259,061, filed Nov. 6, 2009, which is incorporated herein by reference.

BACKGROUND

Chronic bacterial infections remain a significant cause of morbidity and mortality in human and animal populations. Current research efforts focus on generating effective preventative measures through vaccine development and on developing new antimicrobial agents to overcome rapidly increasing numbers of resistant microbes. Despite these efforts, the overall incidence of antibiotic resistance associated with chronic bacterial diseases continues to rise.

Intracellular pathogens, such as *Mycobacterium, Salmonella, Chlamydia, Borrelia, Rickettsia*, and *Brucella*, are particularly difficult to treat because they infect an intracellular niche inside of cells that protects them from being exposed to extracellular host defenses and high concentrations of antibiotics.

A specific example of a difficult to treat intracellular microbial pathogen is *Brucella* spp. *Brucella* are facultative intracellular pathogens of humans and domestic animals. Human brucellosis is strictly zoonotic and manifests as a chronic, debilitating disease from which there is no protective immunity. Brucellosis in humans is considered the most common zoonotic infection worldwide. Human brucellosis has emerged in new areas of the world, particularly in central Asia, while numbers of cases in endemic areas have not been reduced.

Despite the successful use of live-attenuated strains for vaccination in animals, no human vaccine is available for human brucellosis, and vaccine strains approved for use in animals are pathogenic to humans. These disease characteristics contribute to the bacterium being listed as a Category B Bioterrorism Agent. A key to *Brucella* pathogenesis is the organism's ability to survive and replicate within host monocytes and macrophages. Virulent *Brucella* prevents the fusion of phagosomes with lysosomes. The bacteria then replicate in a secondary intracellular compartment that is not acidic and that is removed from normal vesicle trafficking pathways.

Antibiotic resistance is not a hallmark of persistence within the host for intracellular pathogens compared to extracellular pathogens. A remarkably small number of bacteria have adapted to survive and replicate within monocytes and macrophages by modifying the partitioning of the subcellular compartments within the infected cell to avoid degradation and go on to replicate. The adaptation to the intracellular environment provides protection by sequestration from most immune defenses. Species of several genera have adapted in such a manner, including *Mycobacterium, Yersinia, Francisella, Brucella, Burkholderia, Salmonella, Bordetella*, and *Erhlichia*. During the chronic stage of Brucellosis, the bacteria persist and replicate in tissue resident macrophages. Reaching bactericidal concentrations in intracellular environments has proven very difficult using currently used methods. Standard antibiotic regimens for treatment of Brucellosis often require two to three antibiotics given simultaneously for a minimum of 6 weeks. These regimen are difficult to follow and are often ineffective, and patient compliance is a significant problem.

Accordingly, new antimicrobial formulations are needed, such as formulations that can target and/or deliver antimicrobial agents to the intracellular environment of cells infected with bacterial pathogens. Antimicrobial formulations that provide enhanced bactericidal activity are also eagerly sought. Compositions and methods that render antibiotics effective during the chronic stages of a disease are also needed in the art.

SUMMARY

Polyanhydride particles (PA particles) such as microspheres and nanospheres can elicit unique cellular responses from immune cells. The PA particles stimulate internalization, direct intracellular trafficking and degrade slowly within the cells. Antimicrobial compounds can be encapsulated into PA particles, thereby allowing for the compounds to be slowly released after they are internalized by cells as the particle slowly degrades by surface erosion. Varying the type of copolymer constituents of the particle effects particle degradation and can alter the fate of the particle within cells.

Microbial pathogens survive within host tissues by protecting themselves against immune defenses. For example, intracellular pathogens evade host defenses by adapting themselves to the environment within cells, which allows the pathogens to escape contact with antibiotics. PA particles can enter host cells and deliver antibiotics to the same microenvironment of the pathogen. The highly effective targeting of the intracellular environment by PA particles greatly reduces the amount of antibiotic needed to treat such an infection. PA particles also provide delayed and slow release of the encapsulated drug. As described herein, PA particles (nanospheres) that have encapsulated doxycycline with either 1.5% or 3% loading effectively kill intracellular pathogens, including laboratory and field strains of *Brucella canis* and laboratory strains of *Escherichia coli*, as determined by agar disk diffusion assays.

Accordingly, the invention provides a polyanhydride microparticle or nanoparticle that contains a plurality of antimicrobial agents inside the particle; wherein the polyanhydride nanoparticle comprises anhydride copolymers of a 1,ω-bis(carboxy)($C_2$-$C_{10}$)alkane and a 1,ω-bis(carboxyphenoxy)($C_2$-$C_{10}$)alkane. The nanoparticle can be substantially spherical in shape and can have an average diameter of about 100 nm to about 900 nm. When the particle is a microparticle, the microparticle can be substantially spherical in shape and can have an average diameter of about 900 nm to about 5 μm.

The 1,ω-bis(carboxy)($C_2$-$C_{10}$)alkane can be sebacic anhydride (SA), 1,8-bis(carboxyphenoxy)-3,6-dioxaoctane (CPTEG) anhydride, or a combination thereof. The 1,ω-bis(carboxyphenoxy)($C_2$-$C_{10}$)alkane can be, for example, 1,6-bis-(p-carboxy-phenoxy)hexane (CPH). The polyanhydride nanoparticle is formed from anhydrides of these components for form copolymers. The ratio of 1,ω-bis(carboxy)($C_2$-$C_{10}$) alkane to 1,ω-bis(4-carboxyphenoxy)($C_2$-$C_{10}$)alkane in the nanoparticle can be about 90:10 to about 50:50 to about 10:90, or any ratio in between, such as 85:15, 80:20, 75:25, 70:30, 60:40, or 55:45, or the reverse of such ratios.

In certain specific embodiments, the 1,ω-bis(carboxy)($C_2$-$C_{10}$)alkane is sebacic anhydride (SA) and the 1,ω-bis(carboxyphenoxy)($C_2$-$C_{10}$)alkane is 1,6-bis-(p-carboxyphenoxy) hexane (CPH). The 1,ω-bis(carboxy)($C_2$-$C_{10}$)alkane can also be 1,8-bis(carboxyphenoxy)-3,6-dioxaoctane (CPTEG) and the 1,ω-bis(carboxyphenoxy)($C_2$-$C_{10}$)alkane can be 1,6-bis-(p-carboxyphenoxy)hexane (CPH). The antimicrobial agent can be doxycycline or another antimicrobial agent, as described below. The nanoparticle can further include a second antimicrobial agent, as described below.

The invention also provides a method to treat a microbial infection in an animal. The method can include administering to an animal in need of such treatment an effective antimicrobial amount of a composition that includes polyanhydride microparticles or nanoparticles that contain one or more antimicrobial agents. The composition can include the antimicrobial polyanhydride particles and, for example, a pharmaceutically acceptable excipient, diluent or carrier.

The polyanhydride microparticles or nanoparticles can comprise copolymers of, for example, sebacic anhydride (SA) and 1,6-bis-(p-carboxyphenoxy)hexane (CPH) anhydride. The microparticles or nanoparticles then accumulate in infected monocytes, dendritic cells, or both, and degrade by surface erosion over a period of time to release the antimicrobial agents; so as to treat the microbial infection.

The microbial infection can be an infection that causes a chronic disease. For example, the infection can be a bacterial infection. The bacterial infection can be caused by, for example, bacteria of the genera *Bordetella, Borrelia, Brucella, Burkholderia, Chlamydia, Erhlichia, Francisella, Mycobacterium, Rickettsia, Salmonella*, and/or *Yersinia*. The microbial infection may be one that causes Bacterial meningitis, Brucellosis, Erhlichiosis, Glanders, Johne's, mastitis, *Legionella, Lyme disease, Mycobacteria* disease complex, Mycoplasmosis, Q-fever, Salmonellosis, Shigellosis, or Tuberculosis.

In one embodiment, the antimicrobial agent can be doxycycline, optionally in the presence of a second agent, such as bacillomycin. Other antimicrobial agents are further described below. In some embodiments, the polyanhydride microparticles or nanoparticles can encapsulate an average of about 1 µg to about 12 µg of the antimicrobial agent per particle. The polyanhydride microparticles or nanoparticles further comprise an additional antimicrobial agent. The additional antimicrobial agent can be any other suitable agent, for example, a different type of antimicrobial agent, a therapeutic small molecule (e.g., an antimicrobial agent of less than 2 kDa) or a heavy metal. Examples of heavy metal therapeutic agents include copper, iron, aluminum, zinc, gold, compound and ions thereof, and various combinations thereof.

The invention also provides a method to deliver antimicrobial agents to cells infected with microbes comprising contacting cells infected by microbes with an effective amount of a composition comprising polyanhydride microparticles or nanoparticles that encapsulate a plurality of antimicrobial agents;
wherein the polyanhydride microparticles or nanoparticles comprise copolymers of sebacic anhydride (SA) and 1,6-bis-(p-carboxyphenoxy)hexane (CPH) anhydride; and
wherein the microparticles or nanoparticles accumulate in the cells infected by microbes, and degrade by surface erosion over a period of time to release the antimicrobial agents; thereby inhibiting the replication of the microbes, killing the microbes, or both.

The invention further provides improved delivery of antimicrobial agents, such as antibiotics, into host cells that contain pathogens, compared to known delivery systems. Prior attempts to use packaged antibiotics have failed to kill pathogens more effectively than free antibiotics alone (e.g., treatment by standard therapy).

The invention also provides greatly enhanced uptake of PA particles compared to PLGA micro- or nanospheres. Base catalyzed degradation increases the particle longevity within tissues and cells, leading to longer release profiles of bioavailable antimicrobial agents. The PA particles also provide greater encapsulation of hydrophobic antibiotics compared to hydrophilic PLGA-based particles. The acidic compartment provided by hydrophilic PLGA-based particles is detrimental to most antibiotics. However, the PA particle interior is significantly less acidic, thereby providing an encapsulated environment for antimicrobial agents that is much less acidic than PLGA-based particles, which is therefore less detrimental to many kinds of antimicrobial agents than PLGA-based particles.

The chemistry of polyanhydride particles modulate cellular responses that specifically effect cellular uptake, vesicular trafficking and delivery to intracellular organelles. These factors contribute to the type of microenvironment that forms around internalized particles as well as the subsequent release of the antibiotic resulting from the breakdown of the polymerized subunits within the particles themselves. Thus, the chemistry of particles (e.g., the hydrophobicity of the particle interior) serves as an excellent delivery vehicle environment for antibiotics because the chemical properties modulate uptake and aid the determination of the particles' fate within the cell. These particles can be embedded with current antibiotics already approved as treatments for numerous diseases. Loading of antimicrobial agents into PA particles does not chemically modify the antibiotics or negate their antimicrobial function.

For example, cargo loaded PA particles can penetrate and localize to the intracellular compartment occupied by *Mycobacterium paratuberculosis* using tissue culture cells previously infected with the bacteria. Such localization significantly increases the effectiveness of the cargo, thereby reducing the amount of antimicrobial agent necessary to treat the infection.

Experimental observations reveal that the polyanhydride particles distribute inside cells in a similar pattern to that observed for several intracellular pathogens. Thus, the intracellular trafficking of pathogens allowed for the recognition that polyanhydride particles can be used to deliver antimicrobial agents to a pathogen's previously safe intracellular compartment to eliminate the pathogen from the host entirely. The PA particles described herein can therefore be used to treat human diseases, such as Tuberculosis, Brucellosis, Lyme disease, Shigellosis, Q-fever, Glanders, *Legionella, Erhlichiosis, Salmonellosis*, and Bacterial meningitis, as well as the corresponding infections in other animals, including but not limited to Brucellosis, Mycoplasmosis, Johne's, mastitis, *Mycobacteria* disease complex, and Bacterial meningitis.

The invention therefore provides antimicrobial agents encapsulated in nanospheres. The nanospheres can enter the intracellular environment of infected cells. The formulations described herein provide for improved intracellular targeting and release of encapsulated antimicrobial agents within infected cells, such as *Brucella* infected cells, leading to enhanced antimicrobial activity. This increase in antimicrobial activity can make antibiotics significantly more effective during the chronic stages of a disease when most patients begin showing clinical symptoms, leading them to seek medical attention. Once the chronic stage is reached, use of a single antibiotic to treat the disease most often fails to eliminate pathogen from the host. Antimicrobial agents can be effectively targeted to specific intracellular niches of various intracellular pathogens using the polyanhydride nanospheres described herein.

The invention provides for the use of the compositions described herein for use in medical therapy. The medical therapy can be treating infections, for example, bacterial, fungi, algal, or other pathogenic infections. Examples of such infections include Tuberculosis, Brucellosis, Lyme disease, Shigellosis, Q-fever, Glanders, *Legionella, Erhlichiosis, Salmonellosis*, bacterial sepsis and bacterial meningitis. The invention also provides for the use of a composition as described herein for the manufacture of a medicament to treat microbial infections in animals, for example, mammals, such as humans. The medicament can include a pharmaceutically acceptable diluent, excipient, or carrier.

BRIEF DESCRIPTION OF THE DRAWINGS

The following drawings form part of the specification and are included to further demonstrate certain embodiments or various aspects of the invention. In some instances, embodiments of the invention can be best understood by referring to the accompanying drawings in combination with the detailed description presented herein. The description and accompanying drawings may highlight a certain specific example, or a certain aspect of the invention, however, one skilled in the art will understand that portions of the example or aspect may be used in combination with other examples or aspects of the invention.

FIG. 13 illustrates the viability of intracellular *B. abortus* at 72 hours post-inoculation after treatment with doxycycline solubilized by PBS solution (5% doxycycline in PBS) or encapsulated in various polyanhydride particles (equivalent mass of doxycycline as in PBS solution).

FIG. 14 illustrates the continued antibiotic release by serial disc transfer of polyanhydride particles containing doxycycline, while PBS solubilized doxycycline discs provided no zones of inhibition on day two.

DETAILED DESCRIPTION

Figure 1:
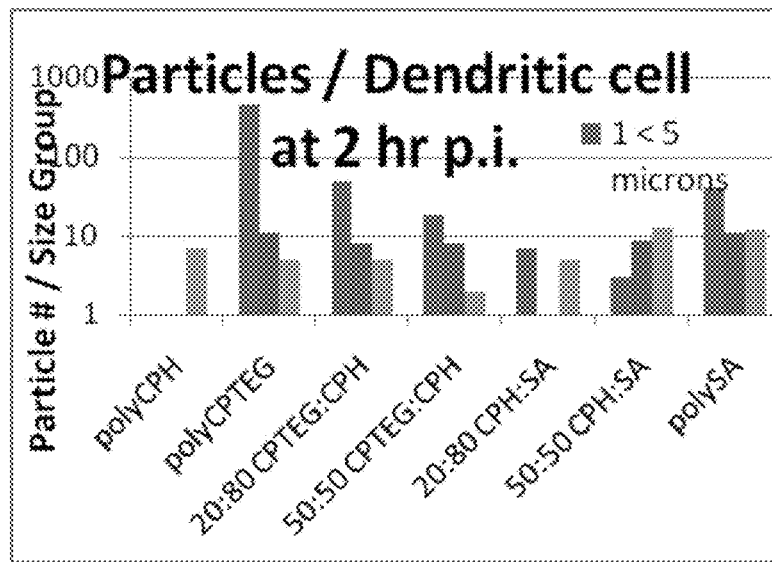
FIG. 1 illustrates two hour counts of particles internalized/ dendritic cell in dendritic cells and monocytes.

The intracellular environment is a privileged site, where the outermost membrane of the host cell prevents large concentrations of solutes, such as antimicrobial agents, present outside the cell from entering the cell. Even once the antimicrobial agents enters a cell, to be an effective therapeutic treatment, the agent must preferably 1) accumulate in a large enough effective dose for, e.g., either bactericidal or bacteriostatic killing; 2) be resistant to inactivation by acidic pH or lysosomal enzymes; 3) deliver or accumulate within the same subcompartment shared with the microbe; 4) lengthen the time of antibiotic activity following a single dose; and 5) must not harm the host.

Encapsulated antimicrobial agents delivered to an infected intracellular environment can improve the intracellular targeting, release, and effectiveness of encapsulated antimicrobial agents within infected cells, such as *Brucella* infected cells, leading to enhanced antimicrobial activity. For example, encapsulated antibacterial agents can be used to delivers the agents to an infected intracellular environment, such as cells infected by *Brucella*, thereby providing an increase in anti-*Brucella* activity. This increased activity can make antibiotics effective during the chronic stages of the disease when most patients present with symptoms and current single antibiotic treatments. Antibiotics can be effectively targeted to the specific intracellular niche of various intracellular pathogens using polyanhydride nanospheres.

Antimicrobial agents encapsulated into polyanhydride (PA) nanospheres can be effective at treating animals persistently infected with microbes, such as *Brucella*. The combination of size and chemistry of the hydrophobic nanospheres synergize to produce a particle that is rapidly internalized and localized to the phagolysosomal compartment, following a pattern of intracellular trafficking very similar to virulent *Brucella*. Within the phagolysosomal vesicle, PA nanospheres persist by resisting bulk degradation under the acidic conditions and slowly release encapsulated antimicrobial agents into the intracellular environment. The PA encapsulation techniques can be used for the effective delivery of a variety of antimicrobial agents (of first, second, third, fourth and subsequent derivative generations) for each group, such as tetracycline, penicillin, sulfa, cephalosporin, aminoglycoside, macrolide, and fluoroquinolone antibiotics; for example, doxycycline, spectinomycin, gentamicin, vancomycin, ciprofloxacin, cephalexin and trimethoprim-sulfamethoxazole.

Intracellular pathogens can cause debilitating and often fatal infections. The infections are frequently chronic and persistent. Infections cause by intracellular pathogens are difficult to treat because the pathogens reside in immune privileged sites within the infected cells. For example, treating *Brucella* infected animals with single or combination antibiotics, even for extended periods of time, typically eliminates only symptoms associated with acute infections. Thus, current treatments for *Brucella* infected animals fall short in eliminating tissue resident bacteria. The treatment methods described herein can eliminate microbes, such as bacteria, that persist intracellularly within tissue resident macrophages during the chronic stages of disease.

*Brucella* infections are difficult to diagnose due to several factors related to the organism's pathogenesis. Such factors include difficulty in quantifying bacteria during a chronic stage, lack of accurate measures of successful treatment, and tissue localization. *Brucella* infection is almost exclusively within tissues where detection of bacteria is very difficult, given the low CFU and transient bacteremia detected in peripheral blood, which is the preferred means for collecting specimens from suspect cases. Additional difficulties include the late onset of a disease (e.g., when patients present), and poor diagnostic tools to assess the bacterial burden. Practitioners often do not know when a treatment has been effective because it is quite difficult to quantify the number of *Brucella* cells at any given time, without harvesting organs.

During the chronic stage of Brucellosis, the bacteria persist and replicate in tissue resident macrophages. This intracellular niche has proven extremely difficult to target effectively with antimicrobial therapy. The delivery of encapsulated antibiotics to the intracellular environment improves intracellular targeting and release of encapsulated antibiotics within *Brucella* infected cells, leading to enhanced bactericidal activity. Targeted intracellular delivery dramatically increases anti-*Brucella* activity during the chronic phase of the disease when most patients present with symptoms. Antibiotics can be effectively targeted to the specific intracellular niche of various intracellular pathogens using polyanhydride nanospheres.

Polyanhydride copolymer nanospheres (PANS) elicit cellular responses from monocytes and dendritic cells that stimulate internalization and direct intracellular trafficking. The PANS can carry cargo such as antimicrobial agents and can release the cargo by slow degradation of the particle within the cells as a form of controlled release. Varying the polymer chemistry of the particle effects particle degradation rates and alters the fate of the particle within cells. PANS are capable of entering host cells and delivering antibiotics in the same microenvironment of the pathogen. This highly effective targeting of the intracellular environment greatly reduces the amount of antibiotic needed to treat such an infection and also provides delayed release.

Definitions

As used herein, certain terms have the following meanings All other terms and phrases used in this specification have their ordinary meanings as one of skill in the art would understand. Such ordinary meanings may be obtained by reference to technical dictionaries, such as *Hawley's Condensed Chemical Dictionary* 14$^{th}$ Edition, by R. J. Lewis, John Wiley & Sons, New York, N.Y., 2001.

References in the specification to "one embodiment", "an embodiment", "an example embodiment", etc., indicate that the embodiment described may include a particular aspect, feature, structure, moiety, or characteristic, but not every embodiment necessarily includes that aspect, feature, structure, moiety, or characteristic. Moreover, such phrases may, but do not necessarily, refer to the same embodiment referred to in other portions of the specification. Further, when a particular aspect, feature, structure, moiety, or characteristic is described in connection with an embodiment, it is within the knowledge of one skilled in the art to affect such aspect, feature, structure, moiety, or characteristic in connection with other embodiments, whether or not explicitly described.

The term "and/or" means any one of the items, any combination of the items, or all of the items with which this term is associated.

The singular forms "a," "an," and "the" include plural reference unless the context clearly dictates otherwise. Thus, for example, a reference to "a compound" includes a plurality of such compounds, so that a compound X includes a plurality of compounds X. It is further noted that the claims may be drafted to exclude any optional element. As such, this statement is intended to serve as antecedent basis for use of such exclusive terminology as "solely," "only," and the like in connection with the recitation of claim elements, or use of a "negative" limitation.

The term "about" can refer to a variation of ±5%, ±10%, ±20%, or ±25% of the value specified. For example, "about 50" percent can in some embodiments carry a variation from 45 to 55 percent. For integer ranges, the term "about" can include one or two integers greater than and/or less than a recited integer. Unless indicated otherwise herein, the term "about" is intended to include values, e.g., weight percents, proximate to the recited range that are equivalent in terms of the functionality of the individual ingredient, the composition, or the embodiment.

As will be understood by one skilled in the art, for any and all purposes, particularly in terms of providing a written description, all ranges disclosed herein also encompass any and all possible subranges and combinations of subranges thereof as well as the individual values making up the range, particularly integer values. A recited range (e.g., weight percents or carbon groups) includes each specific value, integer, decimal, or identity within the range. Any listed range can be easily recognized as sufficiently describing and enabling the same range being broken down into at least equal halves, thirds, quarters, fifths, tenths, etc. As a non limiting example, each range discussed herein can be readily broken down into a lower third, middle third and upper third, etc. As will also be understood by one skilled in the art, all language such as "up to," "at least," "greater than," "less than," "more than," "or more" and the like include the number recited and refer to ranges which can be subsequently broken down into subranges as discussed above. In the same manner, all ratios disclosed herein also include all subratios falling within the broader ratio.

One skilled in the art will also readily recognize that where members are grouped together in a common manner, such as in a Markush group, the present invention encompasses not only the entire group listed as a whole, but each member of the group individually and all possible subgroups of the main group. Additionally, for all purposes, the present invention encompasses not only the main group, but also the main group absent one or more of the group members. The present invention also envisages the explicit exclusion of one or more of any of the group members in the claimed invention.

As will be understood by the skilled artisan, all numbers, including those expressing quantities of ingredients, properties such as molecular weight, reaction conditions, and so forth, are approximations and understood as being modified in all instances by the term "about." These values can vary depending upon the desired properties sought to be obtained by those skilled in the art utilizing the present teachings of the present invention. It is also understood that such values inherently contain variability necessarily resulting from the standard deviations found in their respective testing measurements.

The phrase "one or more" is readily understood by one of skill in the art, particularly when read in context of its usage. For example, one or more substituents on a phenyl ring refers to one to five, or one to up to four, for example if the phenyl ring is disubstituted.

The terms "polyanhydride particle" and "polyanhydride nanosphere" both refer to microparticles and nanoparticles made of polyanhydride polymers as described herein. The polyanhydride polymers of the particles are typically copolymers, such as random mixes of anhydride oligomers (condense prepolymers). The polyanhydride particle can be abbreviated as "PA particle", which can be a microparticle or a nanoparticle. The nanoparticles can also be referred to as polyanhydride nanosphere (PANS).

The group "alkyl" refers to a linear or branched hydrocarbon radical or diradical that is optionally unsaturated and optionally substituted with functional groups as described herein. The alkyl group can contain 1 to about 20 carbon atoms. Typical alkyl groups include, but are not limited to, methyl, ethyl, propyl, isopropyl, butyl, iso-butyl, sec-butyl, tert-butyl, pentyl, 3-pentyl, hexyl, heptyl, octyl, or decyl. In one embodiment, alkyl is preferably $(C_1-C_6)$alkyl. In another embodiment, alkyl is preferably $(C_1-C_4)$alkyl.

In an embodiment where the alkyl group is unsaturated, the alkyl is an alkenyl group or an alkynyl group. Alkenyl can be, for example, vinyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, or 5-hexenyl. The alkenyl can be unsubstituted or substituted. Alkynyl can be, for example, ethynyl, 1-propynyl, 2-propynyl, 1-butynyl, 2-butynyl, 3-butynyl, 1-hexynyl, 2-hexynyl, 3-hexynyl, 1-octynyl, and the like. The alkynyl can be unsubstituted or substituted.

The term "aryl" refers to an aromatic hydrocarbon derived from a parent aromatic ring system. The aryl can be linked to another group at a saturated or unsaturated carbon atom of the parent ring system. The aryl group can have 6 to about 14 carbon atoms. The aryl group can have a single ring (e.g., phenyl) or multiple condensed (fused) rings, wherein at least one ring is aromatic (e.g., naphthyl, dihydrophenanthrenyl, fluorenyl, or anthryl). Typical aryl groups include, but are not limited to, radicals derived from benzene, naphthalene, anthracene, biphenyl, and the like. The aryl can be unsubstituted or substituted as described herein.

The term "halo" refers to fluoro, chloro, bromo, and iodo. Similarly, the term "halogen" refers to fluorine, chlorine, bromine, and iodine.

The term "substituted" is intended to indicate that one or more (e.g., 1, 2, 3, 4, or 5; in some embodiments 1, 2, or 3; and in other embodiments 1 or 2) hydrogen atoms on the group indicated in the expression using "substituted" is replaced with a selection from the substituents described hereinbelow, or with a suitable group known to those of skill in the art, provided that the indicated substituted atom's normal valency is not exceeded, and that the substitution results in a stable compound. Suitable substituent groups include, e.g., alkyl, alkenyl, alkynyl, alkoxy, halo, haloalkyl, hydroxy, hydroxyalkyl, aryl, heteroaryl, heterocycle, cycloalkyl, alkanoyl, alkoxycarbonyl, amino, alkylamino, dialkylamino, trifluoromethylthio, acylamino, nitro, difluoromethyl, trifluoromethyl, trifluoromethoxy, carboxy, carboxyalkyl, keto, thioxo, alkylthio, alkylsulfinyl, alkylsulfonyl, and cyano. The suitable substituent groups can also include, e.g., —X, —R, —OR, —SR, —NR$_2$, —NR$_3$, =NR, —CX$_3$, —CN, —OCN, —SCN, —N=C=O, —NCS, —NO, —NO$_2$, =N$_2$, —N$_3$, NC(=O)R, —C(=O)R, —C(=O)NRR, —S(=O)$_2$OH, —S(=O)R, —S(=O)$_2$R, —OS(=O)$_2$OR, —S(=O)$_2$NR, —OP(=O)(OR)$_2$, —P(=O)(OR)$_2$, —P(=O)(OH)$_2$, —C(=O)R, —C(=O)X, —C(S)R, —C(O)OR, —C(S)OR, —C(O)SR, —C(S)SR, —C(O)NRR, —C(S)NRR, —C(NR)NRR, where each X is independently a halogen ("halo"): F, Cl, Br, or I; and each R is independently H, alkyl, aryl, heterocycle, or a protecting group; or cations or anions thereof. As would be readily understood by one skilled in the art, when a substituent is keto (i.e., =O) or thioxo (i.e., =S), or the like, then two hydrogen atoms on the substituted atom are replaced.

As to any of the above groups that contain one or more substituents, it is understood, of course, that such groups do not contain any substitution or substitution patterns which are sterically impractical and/or synthetically non-feasible. In addition, the compounds of this invention include all stereochemical isomers arising from the substitution of these compounds.

The term "diacid" refers to any group that contains two carboxylic acid (—C(=O)OH) groups. The diacid can be an aliphatic dicarboxylic acid or an aromatic dicarboxylic acid.

An aliphatic dicarboxylic acid is any alkyl group that is substituted with two (or more) carboxylic acid groups. An aromatic dicarboxylic acid is any compound that contains an at least one aryl group and two (or more) carboxylic acids. The two carboxylic acid groups can be on the same aryl group or they can be on different aryl groups. When the two carboxylic acid groups are on different aryl groups, the aryl groups can be linked by a single bond, or then can be linked by other groups, for example, an alkyl group. The alkyl group linking the aryl groups can be optionally substituted and optionally interrupted between carbons with other groups as defined herein.

The term "polymer" refers to a molecule of one or more repeating monomeric residue units covalently bonded together by one or more repeating chemical functional groups. The term includes all polymeric forms such as linear, branched, star, random, block, graft and the like. It includes homopolymers formed from a single monomer, copolymers formed from two or more monomers, terpolymers formed from three or more polymers and other polymers formed from more than three monomers. Differing forms of a polymer may also have more than one repeating, covalently bonded functional group.

The term "polyanhydride" refers to a polymer that is derived from the condensation of carboxylic acids or carboxylic acid derivatives such that repeating units of the resulting polymer are linked by anhydride (—C(=O)—O—C (=O)—) groups. Polyanhydrides can be prepared by condensing diacids or by condensing anhydride prepolymers, as described herein.

The term "carboxylic anhydride" refers to a compound that contains an anhydride (—C(=O)—O—C(=O)—) group. A carboxylic anhydride typically contains only one anhydride group per molecule. Carboxylic anhydrides can be formed by the condensation of two carboxylic acids. Carboxylic anhydrides that can be used in conjunction with the methods described herein include bis-alkyl carboxylic anhydrides, bis-aryl carboxylic anhydrides, and mixed anhydrides. Examples include, but are not limited to acetic anhydride, trifluoroacetic anhydride, and benzoic anhydride. Mixed anhydrides can also be employed, such as acetic benzoic anhydride, which is the condensation product of acetic acid and benzoic acid.

As used herein, an "acyl" group is a group, such as a $(C_1-C_4)$alkyl group, that terminates in a carbonyl radical at its point of attachment to another group. An "acyloxy" group is a substituent, such as a $(C_1-C_4)$alkyl group, that terminates in a carboxyl radical at its point of attachment to another group.

The term "acylated" refers to the conversion of a hydroxyl group into an acyloxy group. Acylation can be carried out by contacting a hydroxyl group or hydroxyl-containing group with a carboxylic anhydride.

As used herein, a "prepolymer" is a monomer, oligomer, or mixture thereof that can be converted into a polymer (e.g., a longer chain polyanhydride). Diacid prepolymers are typically acylated on their terminal carboxy groups. A prepolymer can be, for example, a bis(carboxylic acid acetyl ester), or an anhydride oligomer thereof. In some embodiments, a prepolymer can be a 1,ω-(4-acetoxycarbonylphenoxy)alkane, or an anhydride oligomer thereof. The phenoxy group of the 1,ω-(4-acetoxycarbonylphenoxy)alkane can have ortho, meta, or para substitution patterns.

As used herein, a "homopolymer" is a polymer that is made up of repeating units of one type of monomer. A "copolymer" is a polymer that is made up of repeating units of two or more different types of monomers. In a random copolymer, the organization of the repeating units is random.

The term "contacting" refers to the act of touching, making contact, or of bringing to immediate or close proximity, including at the cellular or molecular level, for example, to bring about a physiological reaction, a chemical reaction, or a physical change, e.g., in a solution, in a reaction mixture, in vitro, or in vivo. For example, a microbe can be killed or inhibited when contacted with an antimicrobial agent.

An "effective amount" refers to an amount effective to treat a disease, disorder, and/or condition, or to bring about a recited effect. For example, an amount effective can be an amount effective to reduce the progression or severity of the condition or symptoms being treated. Determination of a therapeutically effective amount is well within the capacity of persons skilled in the art. The term "effective amount" is intended to include an amount of a compound described herein, or an amount of a combination of compounds described herein, e.g., to treat or prevent a disease or disorder, or to treat the symptoms of the disease or disorder, in a host. Thus, an "effective amount" generally means an amount that provides the desired effect.

The terms "treating", "treat" and "treatment" include (i) preventing a disease, pathologic or medical condition from occurring (e.g., prophylaxis); (ii) inhibiting the disease, pathologic or medical condition or arresting its development; (iii) relieving the disease, pathologic or medical condition; and/or (iv) diminishing symptoms associated with the disease, pathologic or medical condition. Thus, the terms "treat", "treatment", and "treating" extend to prophylaxis and include prevent, prevention, preventing, lowering, stopping or reversing the progression or severity of the condition or symptoms being treated. As such, the term "treatment" includes both medical, therapeutic, and/or prophylactic administration, as appropriate.

The terms "inhibit", "inhibiting", and "inhibition" refer to the slowing, halting, or reversing the growth or progression of a disease, infection, condition, or group of cells. The inhibition can be greater than about 20%, 40%, 60%, 80%, 90%, 95%, or 99%, for example, compared to the growth or progression that occurs in the absence of the treatment or contacting.

The particles described herein can encapsulate a variety of types of cargo by incorporating the cargo molecules into the polyanhydride matrix of the particles. The particles can readily incorporate two or more different types of active agents. Co-agents and/or additives such as dyes and radioactive nuclei may be included in the particles for diagnostic purposes. Other additives can include compounds such as bacillomycin, which can enhance the activity of the active agent. Additionally, bacillomycin can be added to the particle formulation such that it is included inside the particles with a primary active agent, and outside the particle, in the pharmaceutical solution or linked to the particle covalently by a linker such as PEG.

Accordingly, the particles can be loaded with a variety of different active agents. The term "active agent" (and its equivalents "agent," "drug," "bioactive agent," "medicament" and "pharmaceutical") is intended to have the broadest meaning and includes at least one of any therapeutic, prophylactic, pharmacological or physiological active substance, cosmetic and personal care preparations, and mixtures thereof, which is delivered to an animal or plant to produce a desired, usually beneficial, effect. More specifically, any active agent that is capable of producing a pharmacological response, localized or systemic, irrespective of whether therapeutic, diagnostic, cosmetic or prophylactic in nature, is within the contemplation of the invention. Bioactive agents such as pesticides, insect repellents, sun screens, cosmetic agents, and the like may be encapsulated by the particles.

It should be noted that the drugs and/or bioactive agents may be used singularly or as a mixture of two or more such agents, and in amounts sufficient to prevent, cure, diagnose or treat a disease or other condition, as the case may be. The drugs and mixtures thereof can be present in the composition in different forms, depending on which form yields the optimum delivery characteristics. Thus, in the case of drugs, the drug can be in its free base or acid form, or in the form of salts, esters, amides, prodrugs, enantiomers or mixtures thereof, or any other pharmacologically acceptable derivatives, or as components of molecular complexes.

In various embodiments, the active agent can be, for example, an antimicrobial agent. The term "antimicrobial agent" refers to bioactive molecules that kill or inhibit the growth or replication of bacteria, fungi, algae, or other pathogenic organisms, such as tuberculosis. Examples of drugs and antimicrobial agents that can be encapsulated in the particles described herein include the generic and specific agents listed at paragraphs [0057] to [0342] of U.S. Patent Publication No. 2006/0078604 (Kanios et al.), which paragraphs are incorporated herein by reference.

Additional examples of antimicrobial agents include sulfonamides, beta-lactams including penicillin, cephalosporin, and carbepenems, aminoglycosides, quinolones, and oxazolidinones, and metals such as copper, iron, aluminum, zinc, gold, compound and ions thereof, and various combinations thereof. Other agents that can be included in the polyanhydride particles include lipopolysaccharides (LPS), polyguanidines (CPG), bacterial lysates, such as material from a slurry of heat killed *Brucella*, e.g., to form a vaccine, and multi kDa proteins, such as defensins (cysteine-rich cationic proteins comprising about 18-45 amino acids).

The term "microbial infection" refers to an infection in an animal caused by the proliferation of a microbe (a "microorganism") in the animal or within cells or tissue of the animal. The microorganisms can be unicellular or members of a colony of cellular organisms. Examples of microbes include bacteria, fungi, archaea, and protists.

Specific values listed herein for radicals, substituents, ranges, and other described values are for illustration only; they do not exclude other recited values or other values within defined ranges for radicals and substituents in various embodiments. In other embodiments, any recited value or range may be excluded from the scope of an embodiment.

Polyanhydride Prepolymers, Polymers, and Synthesis Thereof.

The polyanhydrides used to prepare the particles of the invention can be prepared as described herein or by methods known to those of skill in the art. Commercial diacids can be used as precursors for preparing prepolymers and the polyanhydrides. Techniques well known to those of skill in the art can also be used to prepare diacids for prepolymer and polyanhydride preparation. Many of these known techniques are elaborated in *Compendium of Organic Synthetic Methods* (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, Jr., 1980; Vol. 5, Leroy G. Wade, Jr., 1984; and Vol. 6, Michael B. Smith; as well as in March, J., *Advanced Organic Chemistry*, 3$^{rd}$ Ed., (John Wiley & Sons, New York, 1985), *Comprehensive Organic Synthesis; Selectivity, Strategy & Efficiency in Modern Organic Chemistry*, in 9 Volumes, Barry M. Trost, Ed.-in-Chief (Pergamon Press, New York, 1993 printing), and Richard. C. Larock, *Comprehensive Organic Transformations*, 2$^{nd}$ Ed., (Wiley-VCH, New York, 1999). A number of examples of methods for the preparation of polyanhydrides are provided below.

A wide range of suitable diacids can be employed to prepare polyanhydrides. The diacid can be a diacid-substituted straight or branched chain alkane that is optionally interrupted by about one to about five -Ph-, —O—, —CH=CH—, and/or —N(R)— groups wherein R is H, phenyl, benzyl, or ($C_1$-$C_6$)alkyl. In one embodiment, the alkane of the diacid can be $C_2$-$C_{12}$(alkyl). In another embodiment, the alkane can be $C_4$-$C_8$(alkyl). Additionally, the alkane group of the diacid can be optionally interrupted by about 1 to about 12 —OCH$_2$CH$_2$O— groups, for example, a poly(ethylene glycol) segment. The alkane group can also be optionally substituted with one, two, or three ($C_1$-$C_6$)alkyl, ($C_1$-$C_6$) alkenyl, trifluoromethyl, trifluoromethoxy, or oxo groups; or combinations thereof.

In one embodiment, a prepolymer can be prepared as illustrated in Scheme 1.

Scheme 1.
Prepolymer Preparation.

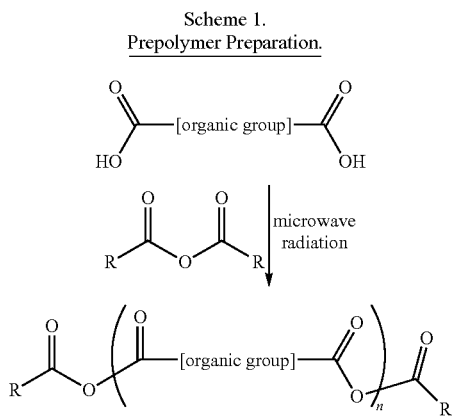

wherein "organic group" is any organic group that can link two carboxylic acid moieties, R is alkyl or aryl, and n is 1 to about 12. Examples of suitable organic groups include, but are not limited to, $C_2$-$C_{12}$(alkyl) groups, -PhO—$C_2$-$C_{12}$ (alkyl)-OPh- groups, and PEG groups having 1 to about 12 PEG units, such as a 3,6-dioxaoctane group. A molar excess of the carboxylic anhydride can be employed. About 2 to about 30 molar equivalents of the carboxylic anhydride can be used. Alternatively, about 5 to about 20 molar equivalents of the carboxylic anhydride can be used. In one embodiment, 6 molar equivalents of the carboxylic anhydride are employed. In another embodiment, 18 molar equivalents of the carboxylic anhydride are employed. The carboxylic anhydride can be, for example, acetic anhydride, trifluoroacetic anhydride, benzoic anhydride, combinations thereof, and/or derivatives thereof.

A prepolymer can also be prepared as illustrated in Scheme 2.

Scheme 2.
Prepolymer Preparation.

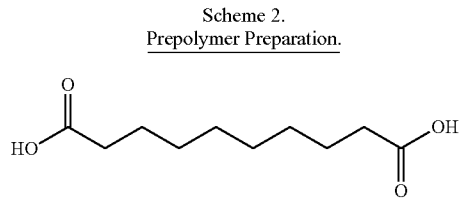

-continued

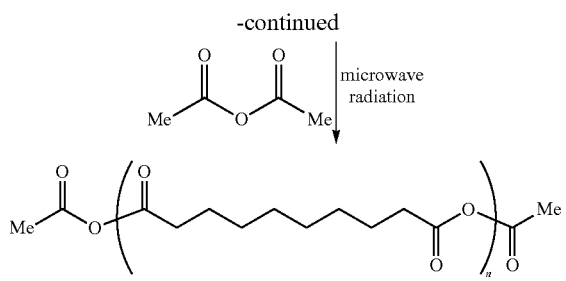

wherein n is 1 to about 12. Other carboxylic anhydrides can be used to form the end groups of the prepolymer, such as, but not limited to, benzoic anhydride. The central aliphatic group can optionally be substituted or interrupted as described herein.

The diacid can also be a 1,ω-bis(carboxy)alkane. As would be recognized by one skilled in the art, alternative nomenclature for a 1,ω-bis(carboxy)alkane is a 1,ω-alkanedioic acid that has two additional carbons in the alkane moiety compared to the corresponding bis(carboxy)alkane.

A prepolymer can also be prepared as illustrated in Scheme 3.

phenyl, benzyl, or $(C_1$-$C_6)$alkyl. In some embodiments, one or both of the aryl groups can be omitted and the carboxy groups are linked by the alkyl chain. In one embodiment, the alkane can be $C_2$-$C_{12}$(alkyl). In another embodiment, the alkane can be $C_4$-$C_8$(alkyl). In another embodiment, the alkane can be one or more PEG groups. Additionally, the alkane group linking the carboxylic acid-substituted aryl groups can be optionally interrupted by 1 to about 12-$OCH_2CH_2O$— groups, for example, a poly(ethylene glycol) segment. The alkane group linking the carboxylic acid-substituted aryl groups can also be optionally substituted with one, two, or three $(C_1$-$C_6)$alkyl, $(C_1$-$C_6)$alkenyl, trifluoromethyl, trifluoromethoxy, or oxo groups; or combinations thereof.

The diacid can be a 1,ω-bis(4-carboxyphenoxy)alkane. In one embodiment, the alkane is a $(C_2$-$C_{10})$alkane. In another embodiment, the alkane can be a $C_4$-$C_8$(alkyl). In certain specific embodiments, alkane can be ethyl, propyl, butyl, pentyl, hexyl, heptyl, octyl, and branched isomers thereof. In one embodiment, the diacid is a 1,6-bis(4-carboxyphenoxy) hexane. In another embodiment, the diacid is a 1,6-bis(carboxy)octane. In another embodiment, the diacid can be a 1,8-bis(carboxyphenoxy)-3,6-dioxaoctane. Mixtures of any Scheme 3.
Prepolymer Preparation.

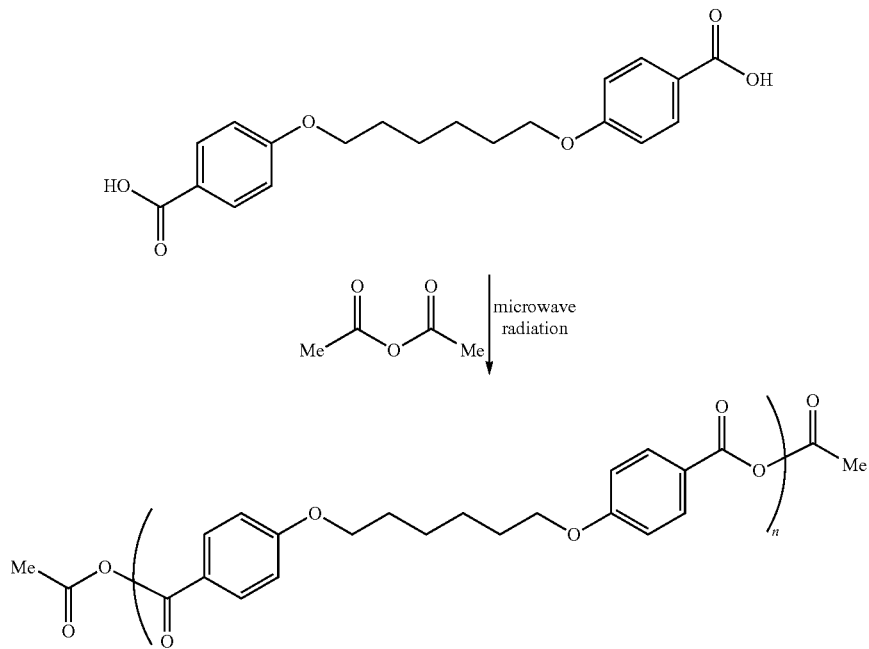

wherein n is 1 to about 12. Carboxylic anhydrides other than acetic anhydride can be used to form the end groups of the prepolymer. The central aliphatic group, the aryl groups, or both, can optionally be substituted, in any combination. The central aliphatic group can also be interrupted as described herein.

Accordingly, the diacid can be two aryl groups that are each substituted with a carboxy group wherein the aryl groups are linked by a straight or branched chain alkane that is optionally interrupted by about one to about five -Ph-, —O—, —CH=CH—, and/or —N(R)— groups wherein R is H, of these diacids can be used in conjunction with the microwave facilitated methods described herein.

Polyanhydrides.

Polyanhydrides can be prepared by condensation methods known in the art or by irradiating a prepolymer with a sufficient amount of microwave irradiation to polymerize the prepolymer. A sufficient amount of microwave radiation can typically be generated by a conventional microwave oven set to 1100 Watts for about 1 to about 30 minutes. More often, a sufficient amount of microwave radiation can be generated in about 1 to about 20 minutes. The resulting polyanhydride can be a homopolymer or a copolymer, depending on the nature of the prepolymer composition used in the reaction.

A polyanhydride can also be prepared by forming a prepolymer in situ from diacids. The diacids can be converted into prepolymers by irradiating diacids in the presence of a carboxylic anhydride. The prepolymer can be prepared by, for example, by irradiating a mixture of (a) a carboxylic anhydride and (b) an aromatic dicarboxylic acid, an aliphatic dicarboxylic acid, or a mixture thereof, with an amount of microwave radiation effective to form the prepolymer. One suitable carboxylic anhydride is acetic anhydride. Other suitable carboxylic anhydrides include, for example, trifluoroacetic anhydride and benzoic anhydride.

The terminal groups of polyanhydrides prepared according to the methods described herein will typically have terminal acyl groups. It is possible for some hydrolysis of the polyanhydrides to occur during the reaction or during the isolation of the polyanhydride. Thus, some terminal groups of such polyanhydrides can be carboxylic acid groups. Accordingly, the methods of the invention include the preparation of polyanhydrides that terminate in acyl groups, carboxylic acid groups, or combinations thereof.

The polyanhydride can be prepared, for example, as illustrated in Scheme 4.

Scheme 4.
Polyanhydride Preparation.

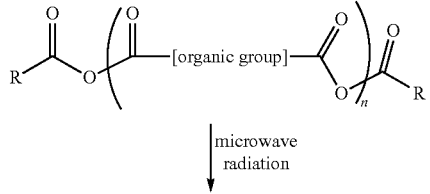

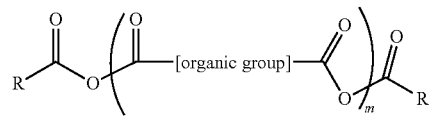

where "organic group" is any organic group that links two carboxylic acid moieties, R is alkyl or aryl, n is 1 to about 12, and m is about 5 to about 200.

The polyanhydride can also be prepared as illustrated in Scheme 5.

Scheme 5.
Polyanhydride Preparation.

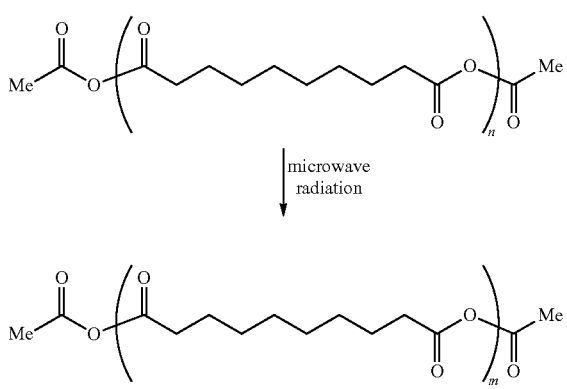

where n is 1 to about 12 and m is about 5 to about 200. In other embodiments, m can be about 10 to about 100, or about 10 to about 50. As would be understood by one skilled in the art, the value of m will typically be larger than the value of n. End groups other than acetate can be used and the central aliphatic group can be optionally substituted or optionally interrupted (e.g., as for PEG groups), or both, as described herein.

The polyanhydride can also be prepared as illustrated in Scheme 6.

Scheme 6.
Polyanhydride Preparation.

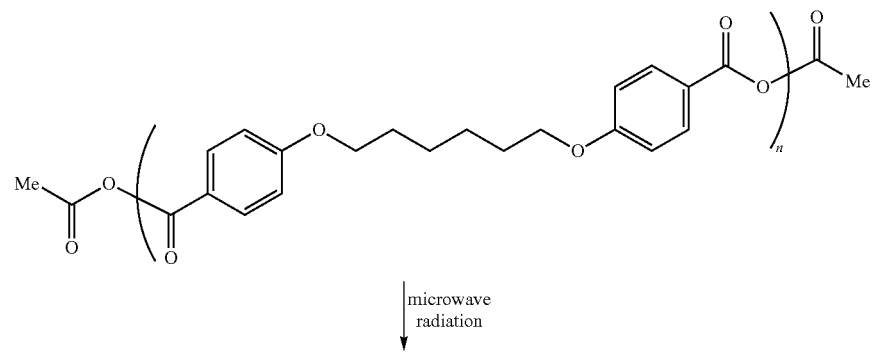

-continued

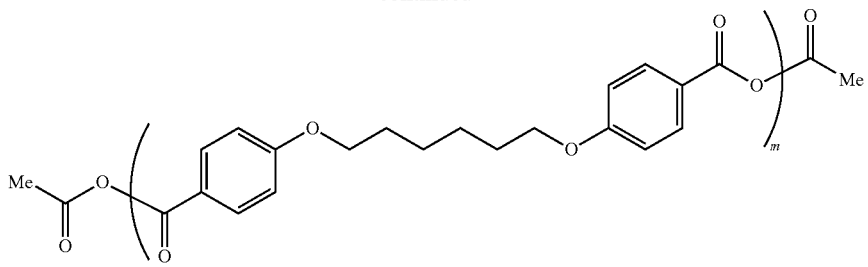

wherein n is 1 to about 12 and m is about 5 to about 100. In other embodiments, m can be about 10 to about 50, or about 15 to about 35. End groups other than acetate can be used and the central aliphatic group, the aryl groups, or both, can optionally be substituted, in any combination. The central aliphatic group can also be optionally interrupted as described herein.

Polyanhydride Polymers for Preparation of Microparticles and Nanoparticles.

A method for preparing the polyanhydride microparticles or nanoparticles includes irradiating one or more diacids, wherein the one or more diacids include an aromatic dicarboxylic acid, an aliphatic dicarboxylic acid, or a mixture thereof, with microwave radiation in the presence of a carboxylic anhydride so as to acylate one or more diacids to yield at least one prepolymer; and irradiating the prepolymer with microwave radiation so as to polymerize said prepolymer to yield the polyanhydride, as a homopolymer or a copolymer.

The prepolymers can be made up of dicarboxylic acids ("diacids") that are acylated at both acid moieties. A prepolymer can be a single acylated diacid unit (monomer), or it can have up to about 12 condensed diacid units. A mixture of different diacids can be employed. The mixture of diacids can yield a random copolymer. The one or more diacids can include a diacid-substituted $C_2$-$C_{12}$ straight or branched chain alkane that is optionally interrupted by about 1 to about 5-Ph-, —O—, —CH=CH—, and/or —N(R)— groups wherein R is H, phenyl, benzyl, or ($C_1$-$C_6$)alkyl. The one or more diacids can also be optionally interrupted by about 1 to about 12-OCH$_2$CH$_2$O— groups. The one or more diacids can also be optionally substituted with 1, 2, or 3 trifluoromethyl, trifluoromethoxy, ($C_1$-$C_6$)alkyl, ($C_1$-$C_6$)alkenyl, or oxo groups, or combinations thereof.

The at least one diacid can be a 1,ω-bis(carboxy)alkane. The at least one diacid can also be a 1,ω-bis(4-carboxyphenoxy)alkane. The alkane can be, for example, a ($C_3$-$C_8$)alkane. Specific examples of the alkane include hexane and octane. The diacid can be 1,6-bis(4-carboxyphenoxy)hexane. Alternatively, the diacid can be 1,6-bis(carboxy)octane (sebacic acid). The at least one prepolymer can also include a bis(carboxylic acid acetyl ester), or an anhydride oligomer thereof. The at least one prepolymer can also include a 1,ω-(4-acetoxycarbonylphenoxy)alkane, or an anhydride oligomer thereof, or a 1,8-bis(carboxyphenoxy)-3,6-dioxaoctane, or an anhydride oligomer thereof.

The carboxylic anhydride can be a bis-alkyl carboxylic anhydride, a bis-aryl carboxylic anhydride, an alkyl-aryl carboxylic anhydride, or a mixture thereof. The carboxylic anhydride can be, for example, acetic anhydride, trifluoroacetic anhydride, or benzoic anhydride. A molar excess of the carboxylic anhydride can be employed. Excess carboxylic anhydride can be removed after the prepolymer has formed.

In various embodiments, the polymers of the microparticles and/or nanoparticles described herein can be poly-sebacic anhydrides (SA), poly-1,6-bis-(p-carboxyphenoxy) hexane (CPH) anhydrides, or poly-1,8-bis (carboxyphenoxy)-3,6-dioxaoctane (CPTEG) anhydrides. In other embodiments, the polymers of the microparticles and/or nanoparticles described herein can be copolymers of sebacic anhydride (SA) and 1,6-bis-(p-carboxyphenoxy)hexane (CPH) anhydride, or copolymers of 1,8-bis(carboxyphenoxy)-3,6-dioxaoctane (CPTEG) anhydride and 1,6-bis-(p-carboxyphenoxy)hexane (CPH) anhydride. The ratio of SA to CPH, or CPTEG to CPH, can be any integer from about 1:19 to about 19:1. An example of a structure of a SA:CPA copolymer is:

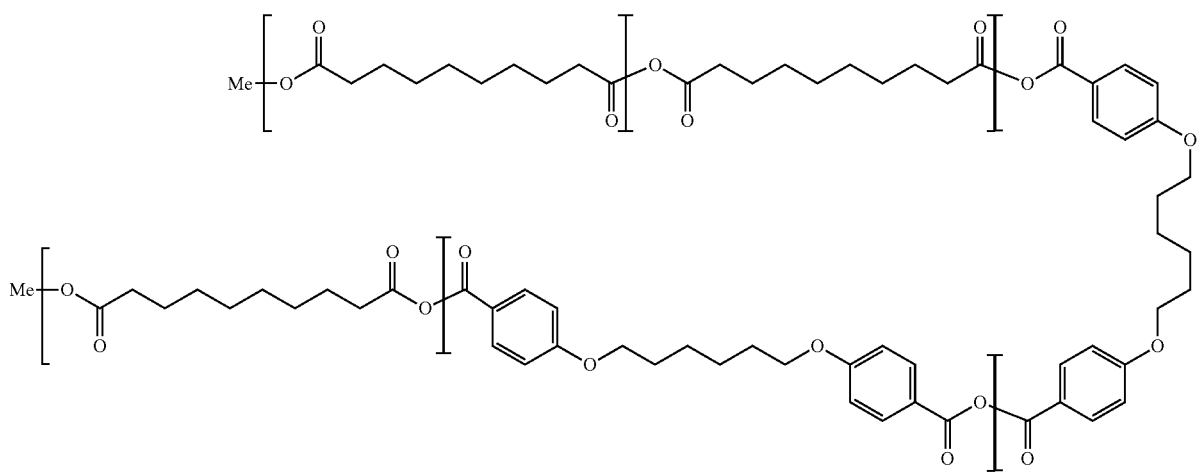

where each block (designated by a single or double bracket) includes a number of repeating units sufficient to provide a polymer with an $M_n$ of about 5,000 to about 50,000 g/mol, such as about 10,000 to about 25,000 g/mol, or about 15,000 to about 20,000 g/mol. The anhydride copolymer can be a block copolymer or a random copolymer, or a combination thereof CPTEG:CPH copolymers can also be prepared to form polymers where each block can include a number of repeating units sufficient to provide a polymer with an $M_n$ of about 5,000 to about 50,000 g/mol, such as about 10,000 to about 25,000 g/mol, or about 15,000 to about 20,000 g/mol.

The PA particles, or polyanhydride nanospheres (PANS), described herein can be loaded with an effective amount of an antimicrobial agent. The PANS have been loaded with doxycycline and numerous model agents. This successful loading indicates that any antimicrobial agent, including both hydrophilic and hydrophobic agents, and be effectively encapsulated without agent deterioration. For example, PA particles (PANS) that have encapsulated doxycycline with either 1.5% or 3% loading kill laboratory and field strains of *Brucella canis* and laboratory strains of *Escherichia coli* by agar disk diffusion assays. Once administered to infected cells, the PANS can localize in intracellular compartments that contain the intracellular pathogen. This localization can occur without killing the host cell that internalized the PANS.

Antimicrobial Polyanhydride Particles.

The polyanhydride particles can incorporate a wide variety of cargo molecules into the matrix of the polyanhydride polymers that make up the particles. Several antibiotics tested in the particles include amikacin, streptomycin, doxycycline, erythromycin, gentamicin, isoniazid, rifampin, and ethambutol. Current loading percentage of antibiotics have been successful up to about 5-10% w/v of copolymer, and higher loading percentages, as high as 50%, can be achieved by techniques such as sequential loading of additional active agent and anhydride polymers to form larger particles. The particles can readily be loaded with about 1 μg to about 12 μg of an antimicrobial agent per particle.

Demonstration of Antimicrobial Activity.

To determine the antimicrobial activity of the PANS, the release kinetics from encapsulated nanospheres can be determined by quantifying the amount of encapsulated antimicrobial agent, such as doxycycline, released from nanospheres. The chemical structure of released antimicrobial agent can be confirmed by analyzing for the presence of derivative molecules by circular dichroism and MS-HPLC. Antimicrobial activity for the released antimicrobial agent can also be confirmed. Results of this analysis can be used to determine the highest amount of encapsulated antimicrobial agent that can be delivered while remaining below host cytotoxicity levels for released antimicrobial agent. This information allows for the determination of optimal antimicrobial agent loading to develop whole animal treatment protocols. In one specific embodiment, the *Brucella* infected cells can be infected with *B. melitensis*. The formulation can be used to eliminate *B. melitensis* residing within macrohpages.

Pharmaceutical Formulations.

The compositions described herein, for example, the polyanhydride particles encapsulating antimicrobial agents, can be used to prepare therapeutic pharmaceutical compositions. The compositions described herein can be formulated as pharmaceutical preparations and can be administered to animal hosts, such as a mammalian host, for example a human patient. The preparation can be provided in a variety of forms. The forms can be specifically adapted to a chosen route of administration, e.g., oral or parenteral administration, intravenous, intramuscular, topical or subcutaneous administration, or administration by inhalation.

The pharmaceutical compositions may be systemically administered in combination with a pharmaceutically acceptable vehicle, such as an inert diluent or an assimilable edible carrier. For oral administration, compositions can be enclosed in hard or soft shell gelatin capsules, compressed into tablets, or incorporated directly into the food of a patient's diet. Compositions may also be combined with one or more excipients and used in the form of ingestible tablets, buccal tablets, troches, capsules, elixirs, suspensions, syrups, wafers, and the like. Such compositions and preparations typically contain at least 0.1% of active compound. The percentage of the compositions and preparations can vary and may conveniently be from about 1% to about 25% of the weight of a given unit dosage form. The amount of active compound in such therapeutically useful compositions is such that an effective dosage level can be obtained.

The tablets, troches, pills, capsules, and the like may also contain one or more of the following: binders such as gum tragacanth, acacia, corn starch or gelatin; excipients such as dicalcium phosphate; a disintegrating agent such as corn starch, potato starch, alginic acid and the like; and a lubricant such as magnesium stearate. A sweetening agent such as sucrose, fructose, lactose or aspartame; or a flavoring agent such as peppermint, oil of wintergreen, or cherry flavoring, may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active composition, sucrose or fructose as a sweetening agent, methyl and propyl parabens as preservatives, a dye and flavoring such as cherry or orange flavor. Any material used in preparing any unit dosage form should be pharmaceutically acceptable and substantially non-toxic in the amounts employed. In addition, the active compound in the particle composition may be further incorporated into sustained-release preparations and devices.

The active agent, e.g., the antimicrobial agent, may be administered in the polyanhydride particles intravenously or intraperitoneally by infusion or injection. Solutions of the pharmaceutical compositions can be prepared in water, optionally mixed with a nontoxic surfactant. Dispersions can be prepared in glycerol, liquid polyethylene glycols, triacetin, or mixtures thereof, or in a pharmaceutically acceptable oil. Under ordinary conditions of storage and use, preparations may contain a preservative to prevent the growth of microorganisms.

Pharmaceutical dosage forms suitable for injection or infusion can include sterile aqueous solutions, dispersions, or sterile powders comprising the compositions adapted for the extemporaneous preparation of sterile injectable or infusible solutions or dispersions. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the maintenance of the required particle size in the case of dispersions, or by the use of surfactants. The prevention of the action of microorganisms can be brought about by various antibacterial and antifungal agents, for example, parabens, chlorobutanol, phenol, sorbic acid, thiomersal, and the like. In many cases, it may be advantageous to include isotonic agents, for example, sugars, buffers, or sodium chloride. Prolonged absorption of injectable compositions can be brought about by agents delaying absorption, for example, aluminum monostearate and/or gelatin.

Sterile injectable solutions can be prepared by incorporating the compositions in the required amount in the appropriate solvent with various of the other ingredients enumerated above, as required, followed by filter sterilization. In the case of sterile powders for the preparation of sterile injectable solutions, methods of preparation can include vacuum drying and freeze drying techniques, which yield a powder of the active ingredient plus any additional desired ingredient present in the previously sterile-filtered solutions.

For topical administration, compositions may be applied in pure form, e.g., in conjunction with a single carrier. However, it will generally be desirable to administer the active agents in the particles to the skin as a composition or formulation, for example, in combination with a dermatologically acceptable carrier formulation, such as a gel, ointment, lotion, foam, or cream.

Useful solid carriers include finely divided solids such as talc, clay, microcrystalline cellulose, silica, alumina, and the like. Useful liquid carriers include water, dimethyl sulfoxide (DMSO), alcohols, glycols, or water-alcohol/glycol blends, in which the compositions can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed using a pump-type or aerosol sprayer.

Thickeners such as synthetic polymers, fatty acids, fatty acid salts and esters, fatty alcohols, modified celluloses, or modified mineral materials can also be employed with liquid carriers to form spreadable pastes, gels, ointments, soaps, and the like, for application directly to the skin of the user. Examples of dermatological compositions for delivering active agents to the skin are known to the art; for example, see Jacquet et al. (U.S. Pat. No. 4,608,392), Geria (U.S. Pat. No. 4,992,478), Smith et al. (U.S. Pat. No. 4,559,157), and Wortzman (U.S. Pat. No. 4,820,508). Such dermatological compositions can be used in combinations with the compositions described herein.

Useful dosages of the compositions described herein can be determined by comparing their in vitro activity, and in vivo activity in animal models. Methods for the extrapolation of effective dosages in mice, and other animals, to humans are known to the art; for example, see U.S. Pat. No. 4,938,949 (Borch et al.). The amount of a composition required for use in treatment will vary not only with the particular active and encapsulating polymer, but also with the route of administration, the nature of the condition being treated, and the age and condition of the patient, and will be ultimately at the discretion of an attendant physician or clinician.

The compositions can be conveniently administered in a unit dosage form, for example, containing 5 to 1000 mg/m$^2$, conveniently 10 to 750 mg/m$^2$, most conveniently, 50 to 500 mg/m$^2$ of active ingredient per unit dosage form. The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

The invention therefore provides therapeutic methods of treating microbial infections in a mammal, which methods involve administering to a mammal having a microbial infection an effective amount of a composition described herein. A mammal includes a primate, human, rodent, canine, feline, bovine, ovine, equine, swine, caprine, bovine and the like.

The ability of a compositions of the invention to treat microbial infections may be determined by using assays well known to the art. For example, the design of treatment protocols, toxicity evaluation, data analysis, quantification of cell kill, and the biological significance of the use of screens are know.

The following Examples are intended to illustrate the above invention and should not be construed as to narrow its scope. One skilled in the art will readily recognize that the Examples suggest many other ways in which the invention could be practiced. It should be understood that numerous variations and modifications may be made while remaining within the scope of the invention.

EXAMPLES

Antibodies and Reagents for Fluorescence Microscopy.

Primary antibodies used for immunofluorescence microscopy were as follows: mouse anti-LAMP 1 monoclonal, anti-mannose-6-phosphate receptor (Iowa State Hybridoma), mouse anti-EEA1, anti-calnexin, anti-BiP/GRP74, anti-p115, anti-p230, anti-SRP54, anti-Rab5 (Transduction Laboratories), mouse anti-Transferrin Receptor (Molecular Probes), rabbit anti-*Brucella* antibody (Difco), rabbit anti-*E. coli* antibody (Molecular Probes) and mouse/rabbit anti-Cathepsin D (Oncogene). Primary antibodies were used routinely at the concentration of 1/100 except for the following: mouse anti-LAMP-1, 1/20; and mouse anti-mannose-6-phosphate receptor, 1/5. Slow-fade and Prolong antifade mounting solution and Lysotracker Red DND-99 were purchased from Molecular Probes.

Example 1

Preparation of Polyanhydrides and Polyanhydride Nanospheres

Sebacic acid (99%), 4-hydroxybenzoic acid, 1-methyl-2-pyrrolidinone anhydrous (99.5%), 1,6-dibromohexane (98.5%) and fluorescein-isothiocyanate-dextran (FITC-dextran) were purchased from Sigma-Aldrich (Milwaukee, Wis., USA). Other chemicals were purchased from Fisher Scientific (Pittsburgh, Pa., USA) and used as received.

Synthesis of SA and CPH pre-polymers and copolymers was performed as previously described (M. J. Kipper et al., *Biomaterials.* 23(22):4405-4412 (2002); E. Shen et al., *J. Control. Release.* 82(1):115-125 (2002); A. Conix, Poly[1,3-bis(p-carboxyphenoxy)propane anhydride], *Macromolecular Synthesis,* 2:95-98 (1966); and U.S. Pat. No. 7,659,322 (Vogel et al.); each incorporated herein by reference).

The resulting polymers were characterized using $^1$H nuclear magnetic resonance to verify polymer chemistry, gel permeation chromatography to analyze molecular weight, and differential scanning calorimetry to determine glass transition temperature and crystallinity. All properties evaluated showed that the synthesized polymers were within accepted ranges.

Nanosphere Fabrication and Characterization.

FITC-dextran loaded nanospheres were fabricated by polyanhydride anti-solvent nanoencapsulation (PAN), similar to the method reported by Mathiowitz et al. for poly (fumaric acid-co-sebacic acid) polymers (E. Mathiowitz et al., *Nature,* 386(6623):410-414 (1997)). Active agents can be encapsulated into the nanospheres in a similar manner. Polymer (145.5 mg) was dissolved in methylene chloride (5 mL) held at room temperature for poly(SA) and 20:80 CPH:SA, and at 0° C. for 50:50 CPH:SA. FITC-dextran (4.5 mg) was added to the polymer solution and homogenized at 30,000 rpm for 30 seconds to create a suspension. The polymer/fluorescein solution was rapidly poured into a bath of petroleum ether at an antisolvent to solvent ratio of 80:1 held at room temperature (~23° C.) for poly(SA) and 20:80 CPHSA, and −40° C. for 50:50 CPHSA (due to the lower glass transition temperature for 50:50 CPH:SA (12)).

Polymer solubility changes due to the presence of anti-solvent caused spontaneous particle formation. These particles were removed from the anti-solvent by filtration (by aspiration using a Buechner funnel and Whatman #2 filter paper) and then dried overnight under vacuum. The procedure yielded a fine powder with at least 70% recovery. The nanosphere morphology was investigated using scanning electron microscopy (JEOL 840A, JEOL Ltd., Tokyo, Japan). Particle diameter was determined using quasi-elastic light scattering (Zetasizer Nano, Malvern Instruments Ltd., Worcester, UK).

Example 2

Polyanhydride Microspheres and Nanospheres

Existing Technology.

Particle encapsulated antibiotics for treating bacterial infections have been prepared using PLGA microspheres and nanospheres. These delivery systems provide minimal, if any, therapeutic benefit. These poor results are magnified for chronic bacterial diseases such as *Brucella* and *Mycobacterium tuberculosis*.

Poly(D,L-lactide-co-glycolide) (PLGA) microspheres and nanospheres have been prepared for certain drug delivery applications. PLGA microspheres and nanospheres are hydrophilic, and degrade by water hydrolyzed degradation. The rate of degradation increases at acidic pH, and the mechanism of erosion has been determined to be bulk erosion. The relative degradation in tissues is rapid, taking only hours to a few days. For example, 95% of PLGA microspheres were degraded within one week (Lecaroz et al., Poly(D,L-lactide-coglycolide) particles containing gentamicin: pharmacokinetics and pharmacodynamics in *Brucella melitensis*-infected mice. Antimicrob. Agents Chemother. 2007, 51: 1185-1190). Lecaroz and coworkers cited some success in reducing bacteria within the spleens of mice infected with *Brucella melitensis* by reporting that the log # of bacteria were reduced from 6.73 to 5.29. However, the mice were still very much infected. A reduction of this magnitude would not provide a suitable clinical treatment for humans.

TABLE 2 of Lecaroz, 2007. Protective effect of three doses of GEN-loaded microparticles against sublethal infection with *Brucella melitensis* 16M administered intraperitoneally.

| | Results for the following time after administration of last dose[a]: | | | | | |
|---|---|---|---|---|---|---|
| | 1 wk | | | 3 wk | | |
| Treatment | Spleen wt (g) | Log CFU/spleen | Reduction (log) | Spleen wt (g) | Log CFU/spleen | Reduction (log) |
| Untreated | 0.87 ± 0.08 | 6.85 ± 0.17 | 0.00 | 0.93 ± 0.11 | 6.73 ± 0.18 | 0.00 |
| Free GEN | 0.86 ± 0.05 | 6.77 ± 0.12 | 0.08 | 0.83 ± 0.26 | 6.77 ± 0.12 | 0.04 |
| 502H empty Mp[b] | 0.80 ± 0.05 | 6.83 ± 0.16 | 0.02 | 1.04 ± 0.14 | 6.87 ± 0.30 | 0.13 |
| 75:25H empty MP | 0.78 ± 0.28 | 6.80 ± 0.12 | 0.05 | 1.16 ± 0.19 | 6.70 ± 0.18 | 0.04 |
| 502H GEN MP | 0.92 ± 0.07 | 6.44 ± 0.05 | 0.41** | 1.12 ± 0.44 | 6.28 ± 0.09 | 0.45 |
| 75:25H GEN MP | 0.87 ± 0.16 | 6.13 ± 0.08 | 0.72** | 0.70 ± 0.36 | 5.29 ± 1.58 | 1.45** |

[a]Groups of six mice each were infected intraperitoneally with *B. meditensis* 16 M (1 × 10$^5$ CFU/mouse). After 2 weeks, the animals received three doses of free or encapsulated GEN (1.5 mg/kg). At 1 and 3 weeks after administration of the last dose, the animals were killed.
**P < 0.01 (Mann-Whitney U test).
[b]MP, microsphere.

As can be seen from the Lacaroz Table 2, the Lacaroz procedure merely reduced the number of cell forming units and did not treat the bacterial infection to any appreciable or clinically relevant extent.

Examples of Polyanhydride Microspheres and Nanospheres of the Invention.

In various embodiments, polyanhydride microspheres and nanospheres can be copolymerized particles ("copolymer") of a hydrophobic monomer (CPH) and a hydrophilic monomer (either SA or CPTEG). For example, certain polyanhydride nanospheres described herein are based on the monomers sebacic acid (SA), 1,6-bis(p-carboxyphenoxy)hexane (CPH), and/or 1,8-bis(p-carboxyphenoxy)3,6-dioxaoctane (CPTEG). These polyanhydride particles can be used for applications such as drug delivery and/or vaccine delivery.

The polyanhydride particles that include CPH have hydrophobic properties, they resists hydrolytic degradation in vivo, and they resist degradation at acidic pH. They also degrade slowly, and the degradation occurs by a surface erosion mechanism (vs. bulk erosion by PLGA). Encapsulated cargo can thus be slowly released during surface erosion. Very little leaching of cargo from intact particles occurs.

Figure 2:
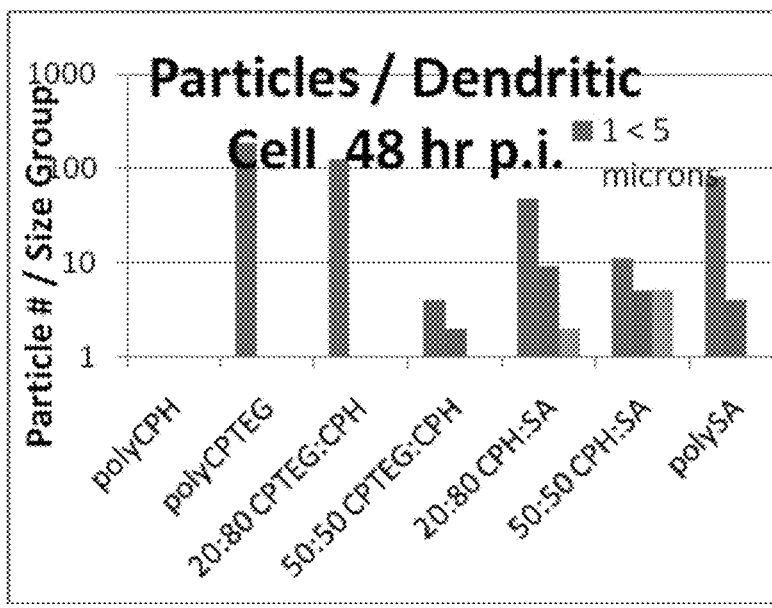
FIG. 2 illustrates 48 hour counts of particles internalized/ dendritic cell in dendritic cells and monocytes.
Figure 3:
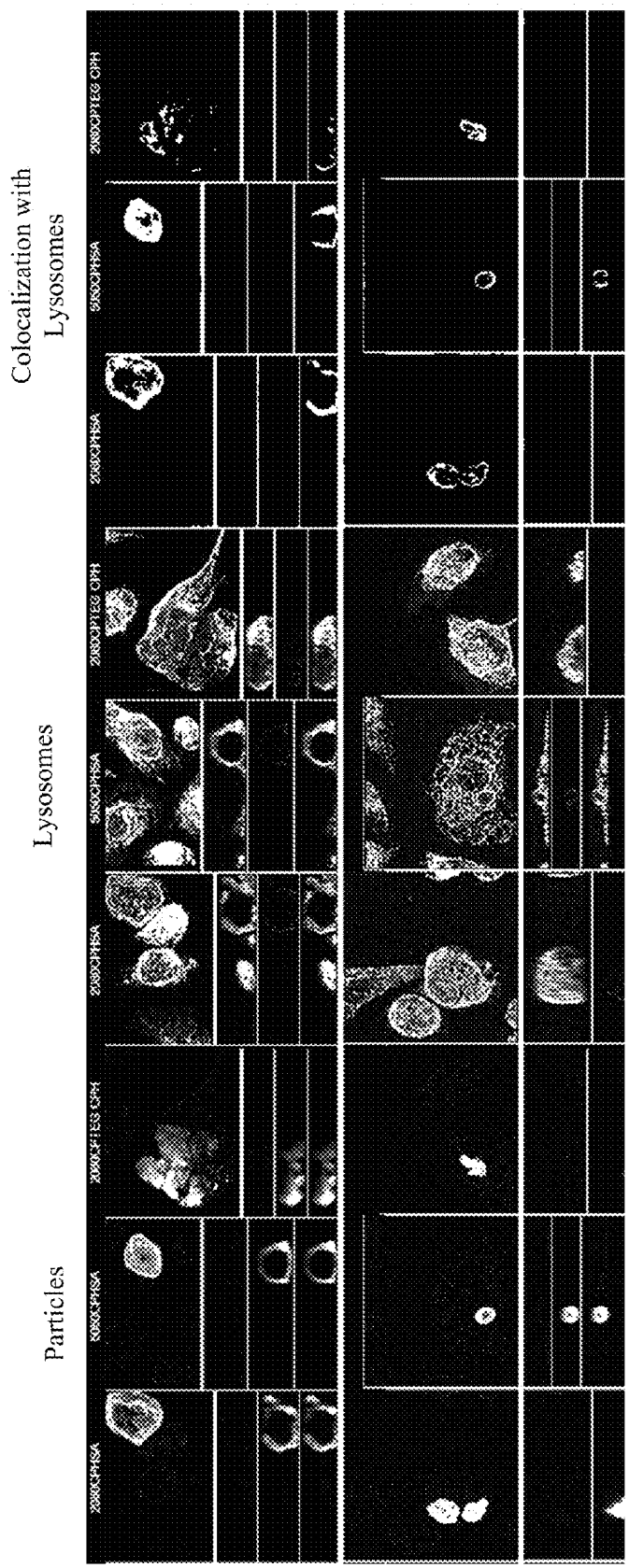
FIG. 3 illustrates intracellular compartment localized to lysosomes by LAMP1 staining
Figure 4:
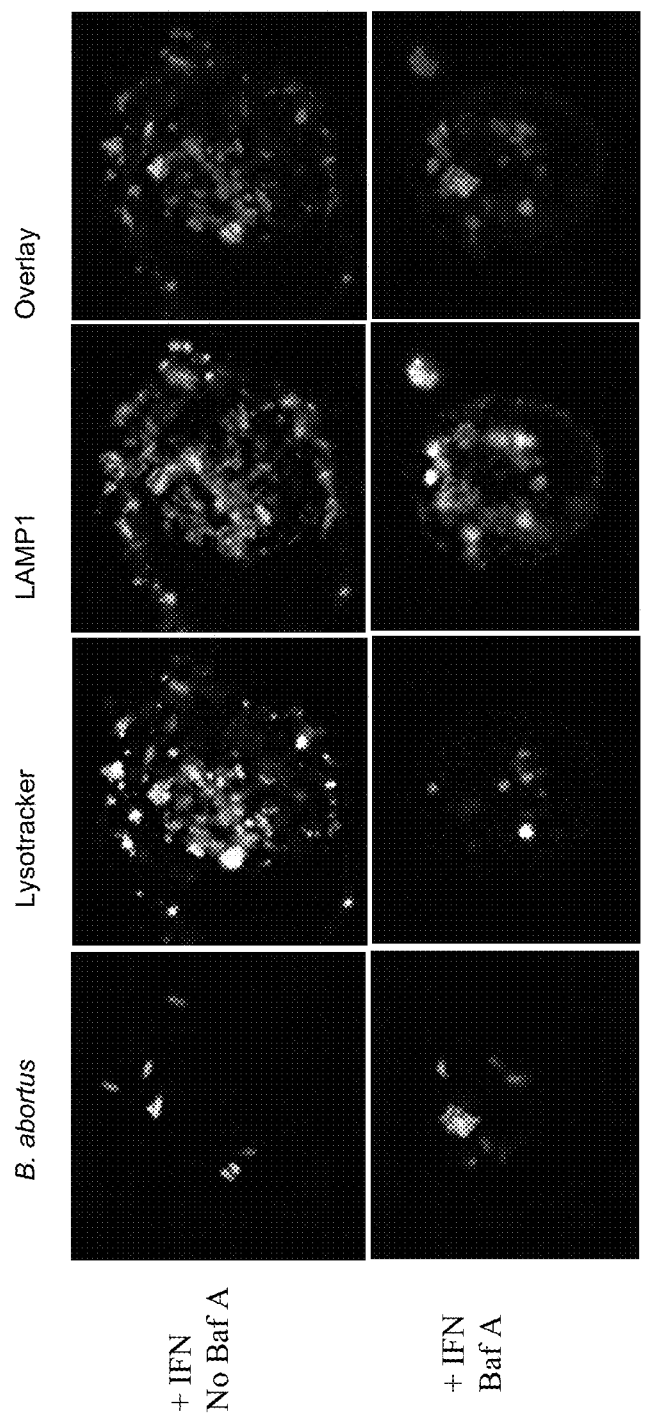
FIG. 4 illustrates intracellular localization of *Brucella abortus* within monocytes (same lineage as dendritic cells).

The relative degradation in tissues is weeks to months, depending on the size and specific polyanhydride used to prepare the particles. Spleens and livers of Mice that have been injected with small numbers of particles had high remaining levels after 1 week (FIG. 1). In dendritic cells and monocytes, two hour counts of particles internalized/dendritic cell are shown in FIG. 1. In dendritic cells, 48 hour counts of particles internalized/dendritic cell are shown in FIG. 2. FIG. 3 illustrates intracellular compartment localized to lysosomes by LAMP1 staining FIG. 4 illustrates intracellular localization of *Brucella abortus* within monocytes (same lineage as dendritic cells). This figure demonstrges that particles and *Brucella* reside within the same intracellular compartment.

Example 3

Intracellular Survival and Replication of *B. Abortus* Strains in THP-1 Cells THP-1 cells used for the evaluation of the intracellular survival and replication profiles of the *B. abortus* strains were plated into 96 well flat bottom tissue culture plates. Bacterial suspensions were prepared generated by scraping 48 hour cultures of the *B. abortus* strains grown on BA into screw cap microfuge tubes containing PBS. Pellets of bacteria were re-suspended by vigorous vortexing and numbers of bacteria present in the suspensions were determined by $OD_{600}$ measurements. Opsonization took place within these dilute suspensions containing either rabbit anti-*Brucella* (Difco) or murine complement component (C3) isolated fresh from non-infected mice. Concentrations of antibody necessary to mediate opsonization without agglutinating the bacterial suspensions were achieved using antibody dilutions ranging from 1/2000 to 1/5000.

Bacterial cell suspensions and antisera were incubated together either at 37° C. in a shaking water bath for 20 minutes or at room temperature for 30 minutes followed by brief vortexing. Suspensions of opsonized bacteria were added to monocyte monolayers at a multiplicity of infection (bacteria: monocyte ratio) 20:1 for *B. abortus* 2308. Tissue culture plates were gently agitated by hand then centrifuged at 4° C. for 10 minutes at 270×g. Monolayers were washed gently with cold PBS to remove non-adherent bacteria then incubated in fresh medium for 20 minutes at 37° C. with 5% $CO_2$ to allow for phagocytosis of adherent bacteria. Monolayers were washed 3 times with PBS to remove any remaining non-adherent bacteria.

Fresh media containing 100 μg/mL gentamicin was added following the last wash step to kill adherent, extracellular bacteria. For experiments lasting longer than 2 hours, the 100 μg/mL gentamicin supplemented medium was replaced with medium containing 10 μg/mL gentamicin after 1 hour and remained in this medium for the duration of the experiment.

Viability of intracellular *Brucella* was determined by lysing monocytes with 0.1% deoxycholate, diluting suspensions in PBS and plating aliquots in triplicate on BA medium (Bellaire, Elzer et al. 1999). Percent survival of bacteria at 24 and 48 hours was calculated based on the number of internalized bacteria detected at 1 hour post infection, which represents 100% of internalized bacteria. Statistical comparisons were made using Student's t-test. Host cell cytotoxicity assays for cultured cells can be recorded using the MTT assay for quantitative measurements and by propidium iodide exclusion for microscopy purposes.

Figure 5:
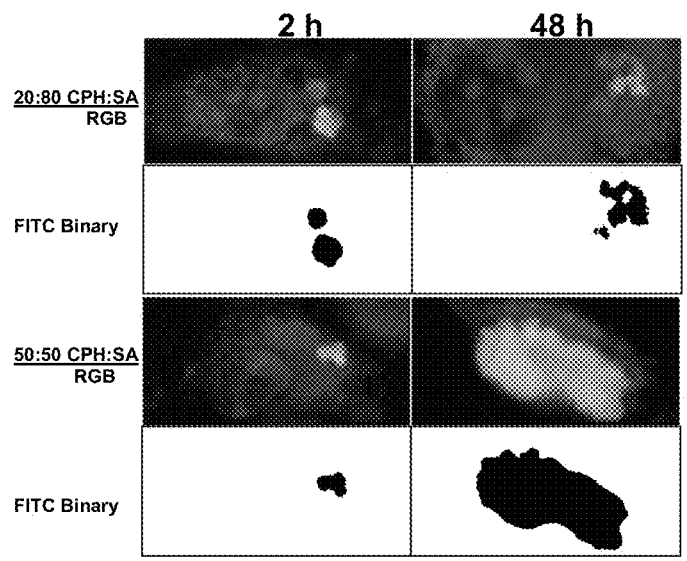
FIG. 5 illustrates quantifying the intracellular stability of nanospheres using morphometric image analysis. Images of FITC-encapsulated nanospheres were captured using 40× objective and processed using constant values for camera exposure and image thresholding throughout the experiment. Images of Lamp1 and nuclei stained dendritic cells incubated with nanospheres at indicated times were background subtracted to generate binary equivalent image (FITC Binary) to perform particle analysis using ImageJ v1.42 software (bar=5 µm).
Figure 6:
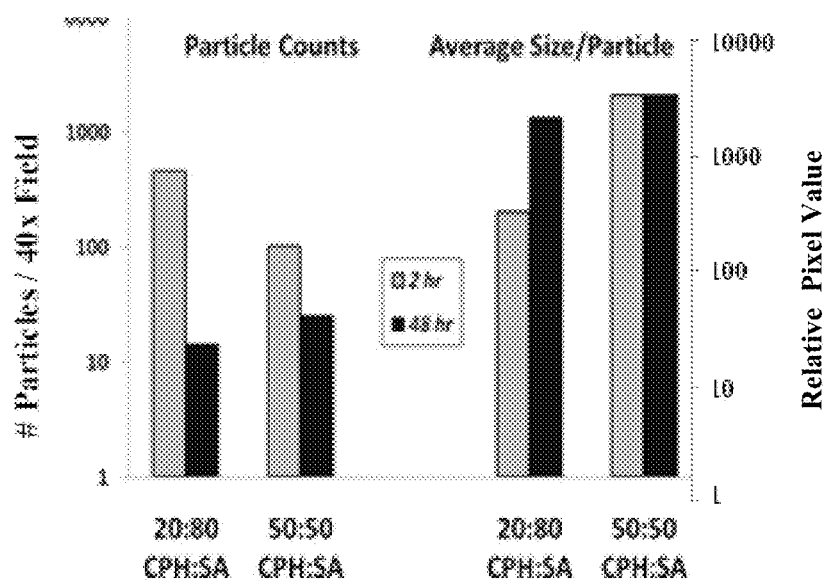
FIG. 6 illustrates binary particle counts and pixel area results as determined from FIG. 1. Binary particle counts and pixel area results were averaged from at least 15 separate fields of view for each time point and particle composition.

FIG. 5 illustrates quantifying the intracellular stability of nanospheres using morphometric image analysis. Images of FITC-encapsulated nanospheres were captured using 40× objective and processed using constant values for camera exposure and image thresholding throughout the experiment. Images of Lamp1 and nuclei stained DC's incubated with nanospheres at indicated times were background subtracted to generate binary equivalent image (FITC Binary) to perform particle analysis using ImageJ v1.42 software (bar=5 μm). FIG. 6 illustrates binary particle counts and pixel area results as determined from FIGS. 1 and 2. Binary particle counts and pixel area results were averaged from at least 15 separate fields of view for each time point and particle composition.

Using information regarding effective concentrations determined above, mice can be experimentally infected with virulent *Brucella abortus* strain 2308 (example of chronic infection shown in FIG. 7) and treated with PANS by single dose (~10 μg/kg) i.v. tail vein injection at 4 weeks post infection. The status of the chronic infection within BALB/c mice can be measured by harvesting the spleens and livers of mice at 1 week intervals after infection, the tissues can be homogenized in PBS, serially diluted and plated on Schaedler agar plates supplemented with 5% bovine blood.

Figure 7:
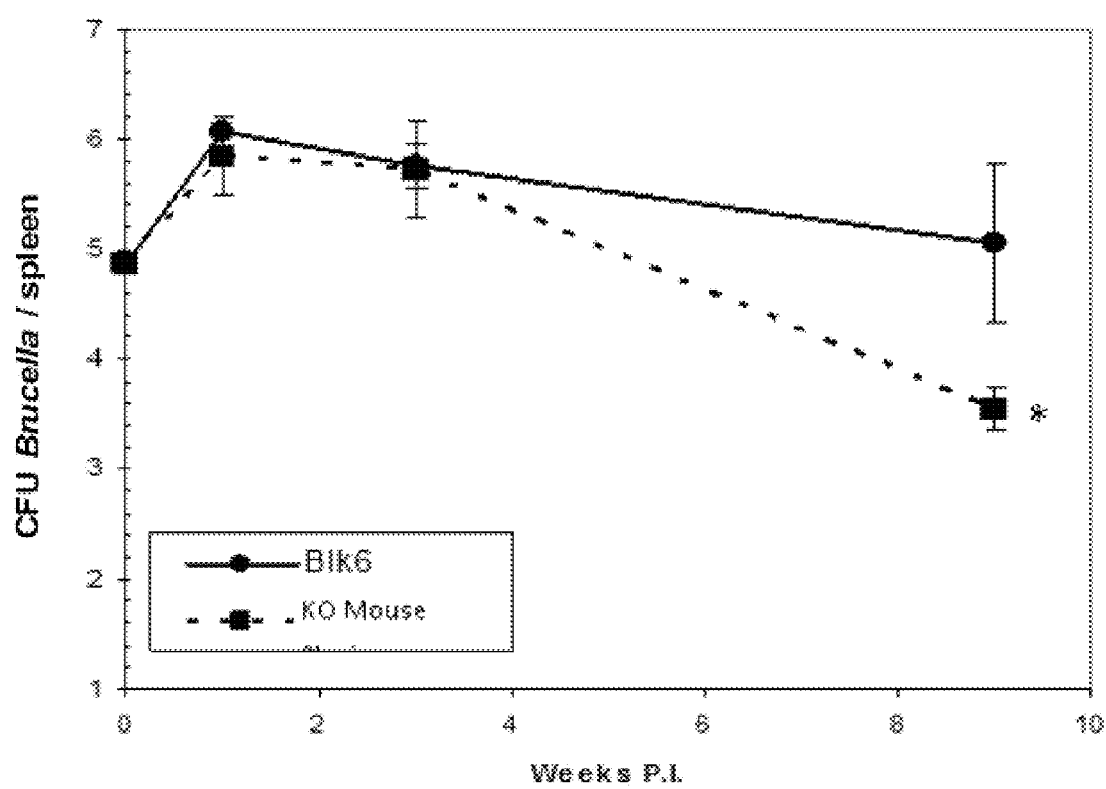
FIG. 7 illustrates a data of chronic infection of Blk6 mice by virulent *Brucella abortus* strain 2308. The experiment illustrates the establishment of infection at 1 week and how it is followed by maintenance of the chronic infection in the spleens of mice infected i.p. with *Brucella*. CFU of *Brucella* recovered from the spleens of these animals are shown as an average of 5 mice per group per time point. Student's T-test indicates that the KO mouse strain has fewer *Brucella*.

BABL/c mice were chosen because they are regarded as being more susceptible to *Brucella* infection, where the bacterial load in the spleen and liver persists at a much higher level than seen in Blk6 mice (Baldwin and Parent 2002). The typical chronic infection includes the "plateau phase" reached at week 2 and extends to 12 weeks and beyond (FIG. 7). Mice are infected i.p. with $1 \times 10^5$ CFU in PBS suspension.

FIG. 7 illustrates an experimental infection of Blk6 mice as indicated above. The representative experiment illustrates the establishment of infection at 1 week and how it is followed by maintenance of the chronic infection in the spleens of mice infected i.p. with *Brucella*. CFU of *Brucella* recovered from the spleens of these animals are shown as an average of 5 mice per group per time point. Student's T-test indicates that the KO mouse strain has fewer *Brucella*, illustrating how changes in *Brucella* colonization can be quantified between different treatment groups. Ad hoc statistical analysis can also include one-way Anova to detect drug specific changes over the entire course of the experiment.

Example 4

Stimulation of Monocytes with Interferon-γ (INF-γ) Inhibits the Intracellular Replication of *Brucella*

The intracellular trafficking and fate of PANS can overlap considerably with the location of *Brucella* containing vesicles in infected macrophages. This can be confirmed using immunofluorescence microscopy to examine the effects of particle chemistry (polymer composition) on PANS internalization, intracellular trafficking, and intracellular compartmentalization. To understand how variations in nanoparticle chemistry impact in vivo anti-*Brucella* activity, microscopic experiments can be carried out to visualize how PANS of different copolymer formulations interact with *Brucella* containing replicative vesicles within murine and human macrophage cell lines.

In Vitro Assessments.

Figure 8:
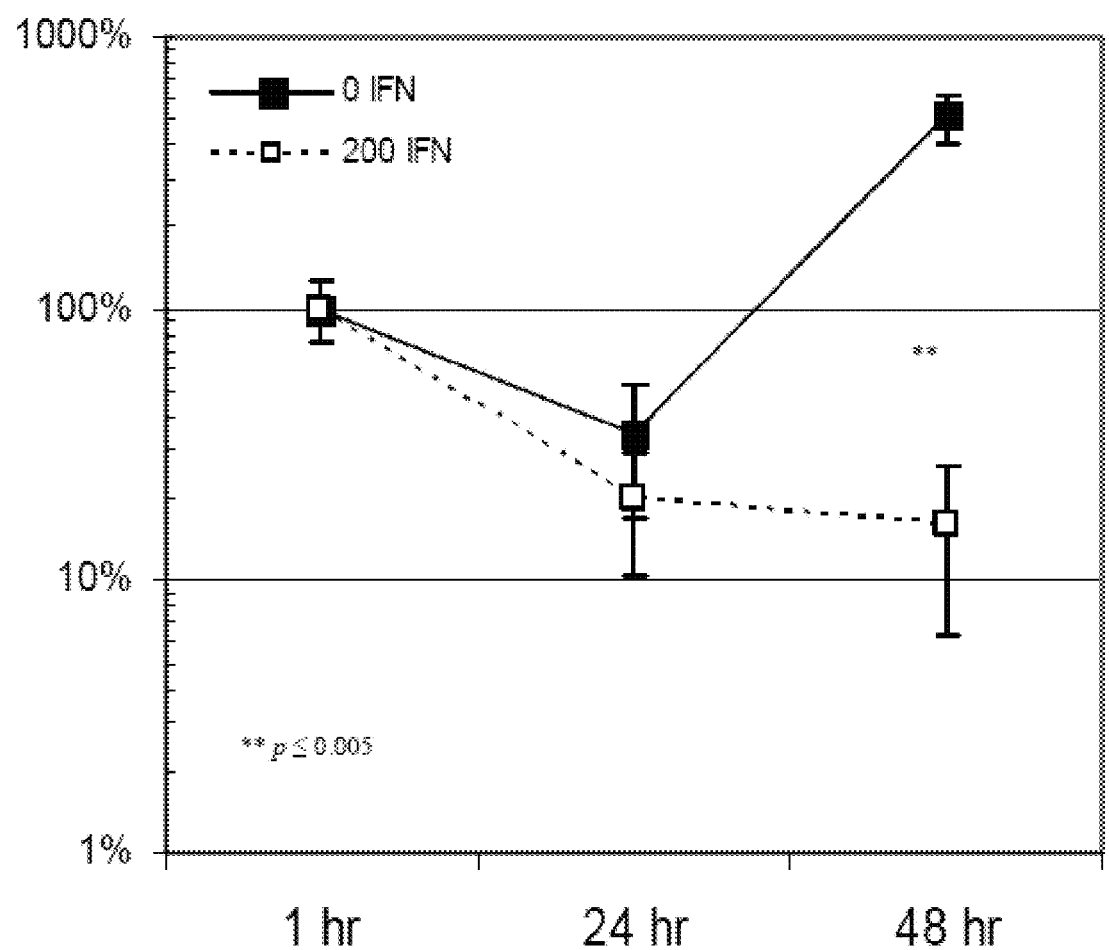
FIG. 8. Stimulation of monocytes with interferon-γ inhibits the intracellular replication of *Brucella*. Adherent THP-1 cells were treated with 200 U/mL of IFN-γ beginning 24 hours prior to infection with opsonized *B. abortus*. Percent survival of intracellular bacteria was determined as described and representative results are shown.

In vitro bacterial survival assays can be carried out, where the number of viable intracellular *Brucella* recovered from monocytes is quantified by colony plating. FIG. 8 reveals the typical survival curve of *Brucella* within monocytes where a significant number of bacteria are killed over the first 24 hour period, while the bacteria continue to replicate over the second 24 hour period. In addition to the human THP-1 monocytic cell line used for bacterial survival assays, parallel experiments can be performed with the murine cell line J774A. Both of these cell lines have been used numerous times in *Brucella* intracellular viability studies and have been shown to accurately model the infection as compared to primary cells (Rittig, Alvarez-Martinez et al. 2001; Bellaire, Roop et al. 2005).

Experiments using J774A cells follow the protocol outlined in Example 3 for THP-1 cells. Results from experiments with THP-1 cells clearly demonstrate that entry of the bacteria and replication within cells, as measured over the course of the 48 hours of infection, are reduced for cultures treated with both soluble doxycycline and doxycycline encapsulated PANS (equivalent of 10 μg/mL for both groups), however the doxycycline encapsulated PANS was significantly more effective.

Example 5

Nanosphere Degradation in Dendritic Cells

Nanosphere degradation in dendritic cells is a strong function of the polymer structure and properties of the nanosphere material. The nanospheres described herein elicits novel phagocytic response from dendritic cells due to the chemical composition of the nanospheres, such as increased hydrophobicity compared to known treatment methods. Reference can again be made to FIG. 5, which illustrates quantifying the intracellular stability of nanospheres using morphometric image analysis. Images of FITC-encapsulated nanospheres were captured using 40× objective and processed using constant values for camera exposure and image thresholding throughout the experiment. Images of Lamp1 and nuclei stained dendritic cells incubated with nanospheres at indicated times were background subtracted to generate binary equivalent image (FITC Binary) to perform particle analysis using ImageJ v1.42 software (bar=5 μm). Also, FIG. 6 illustrates binary particle counts and pixel area results as determined from FIG. 1. Binary particle counts and pixel area results were averaged from at least 15 separate fields of view for each time point and particle composition.

Immature dendritic cells internalize (<2 μm) particles by phagocytosis. The amount of nanoparticles internalized is dramatically lower than observed for PStB polymerized actin localized with the phagosomal cup. Polymerized actin is retained around newly formed phagosomes containing PANS compared to PStB. To analyze the cellular mechanisms driving particle uptake, actin polymerization, lipid raft aggregation, and clathrin deposition can be inhibited.

To determine if nanosphere hydrophobicity affects the fate of particles within dendritic cells (DCs), equivalent amounts of FITC-dextran loaded 20:80 CPH:SA and 50:50 CPH:SA nanospheres were incubated with immature C3H DCs for 30 minutes, then washed to remove extracellular nanospheres. Cultures were incubated with fresh media for an additional 2 or 48 hours to visualize particle uptake (2 hours) and intracellular stability (48 hours) using immunofluorescence microscopy.

Figure 9:
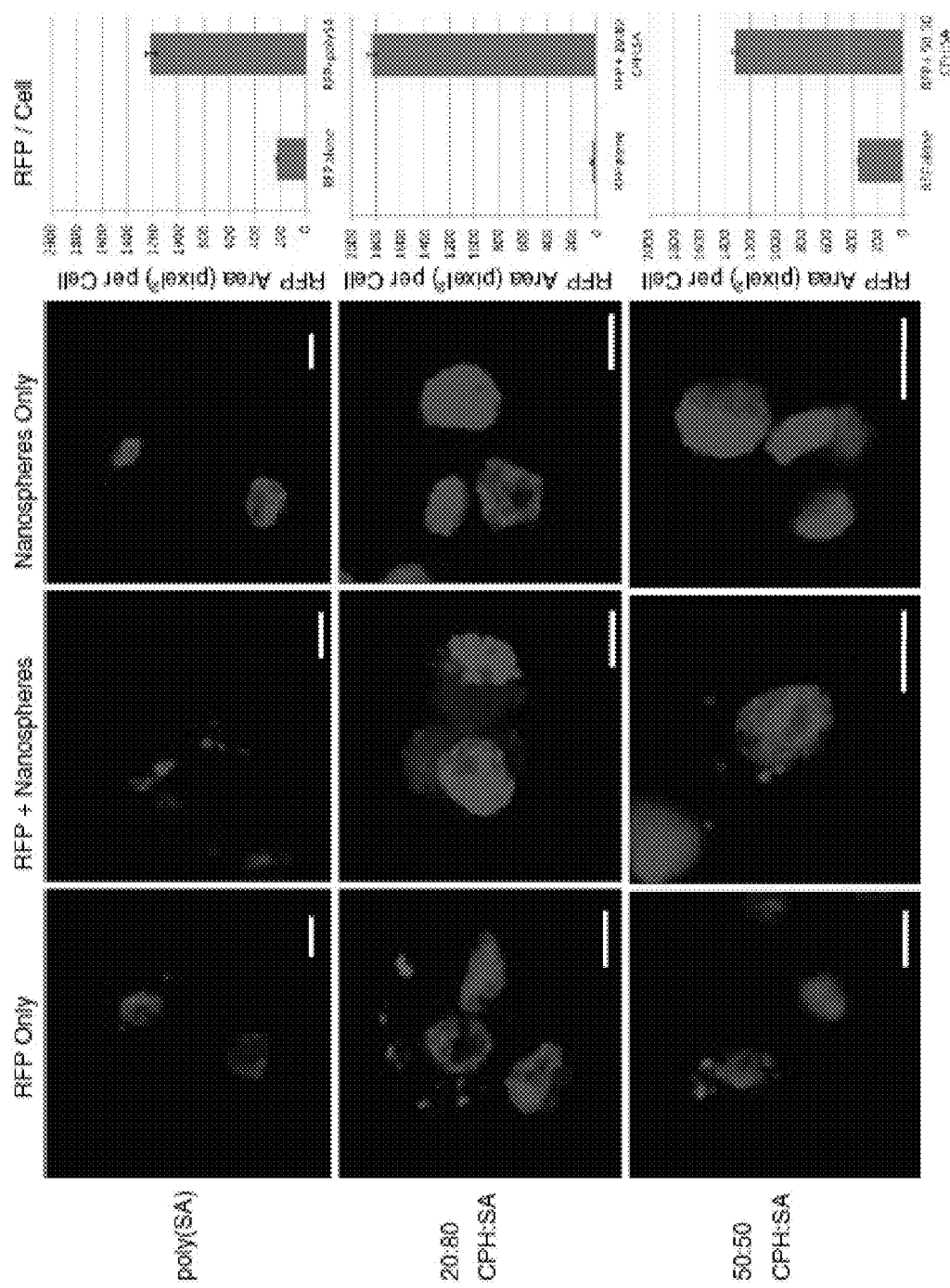
FIG. 9 illustrates the enhanced uptake of soluble Eα-RFP antigen by monocytes (nuclei lighter shade) after co-incubation with polyanhydride nanospheres for 2 hours. Data demonstrated that the poly(SA) nanospheres enhanced antigen internalization more readily than did 20:80 CPH:SA followed by 50:50 CPH:SA. Representative epifluorescent images were captured and processed using identical exposure and ImageJ software settings. Adjacent bar graphs summarize the average amount of RFP detected per cell. Pixel areas within each image correspond to relative intensity of RFP signal detected inside cells. Values from three randomly selected fields of view were used to calculate averages and standard deviation. Scale bar=5 µm.

FIG. 9 illustrates the enhanced uptake of soluble Eα-RFP antigen by monocytes after co-incubation with polyanhydride nanospheres for 2 hours. Data demonstrated that the poly(SA) nanospheres enhanced antigen internalization more readily than did 20:80 CPH:SA followed by 50:50 CPH:SA. Representative epifluorescent images were captured and processed using identical exposure and ImageJ software settings. Adjacent bar graphs summarize the average amount of RFP detected per cell. Pixel areas within each image correspond to relative intensity of RFP signal detected inside cells. Values from three randomly selected fields of view were used to calculate averages and standard deviation. Scale bar=5 μm.

Polyanhydride Nanospheres Enhance Antigen Internalization.

It was demonstrated that polymer chemistry significantly influences the uptake of a model antigen (Ea tagged with red fluorescent protein (RFP), henceforth referred to as Eα-RFP), by THP-1 human monocytic cells. The THP-1 cells were co-incubated with blank nanospheres (poly(SA), 20:80 CPH:SA, or 50:50 CPH:SA) and soluble Eα-RFP.

In order to evaluate phagocytic processes, the nanospheres were co-incubated with the THP-1 cells for 30 minutes. Cultures were washed and the cells were placed back in the incubator for 2 hours prior to analysis. In order to evaluate endocytic processes, the nanospheres were co-incubated with the THP-1 cells for 6 hours. Cultures were washed and the cells were placed back in the incubator for 48 hours prior to analysis. The cells were fixed and visualized by epifluorescence microscopy employing TRITC/rhodamine filter set with 510-560 nm excitation and 575-645 nm emission. Image black levels for the RFP protein were set using cells not incubated with RFP. Exposure times for RFP detection were kept constant throughout the experimental groups to facilitate accurate comparative analysis. Bar graphs of the relative pixel intensity of internalized RFP were calculated from RAW-RFP images using the ImageRplugin/histogram function.

These bar graphs reveal the relative pixel intensity of the RFP protein detected in the presence and absence of nanospheres. Representative photomicrographs and bar graphs summarizing cell associated RFP data are provided in FIG. 9. Comparisons among the three chemistries reveal that after 2 hours of co-incubation, all three chemistries dramatically increased the amount of soluble antigen internalized by monocytes.

A potential mechanism for the increase in uptake stimulated by the nanospheres is that the protein itself is able to adsorb on the surface of nanospheres that are then subsequently internalized by the APC. However, control experiments failed to detect soluble RFP adsorbing onto FITC-labeled nanospheres and culture conditions include ample amounts of serum proteins present in the 10% fetal bovine serum supplemented medium. This data demonstrates that the chemistry of the polyanhydride nanospheres influences the ability of APCs to internalize soluble antigen.

These studies indicate that the chemistry of the carrier has a significant effect on protein stability. Ova has a tendency to form moisture-induced covalent aggregates, which is shown by the presence of characteristic bands between 54 and 97 kDa (lane 2), in addition to the major Ova band at 48 kDa (data not shown). Strongly antigenically reactive bands are visible for both states, which was comparable to the unencapsulated Ova, for the protein released from each of the CPTEG-containing polymers (lanes 6-8), indicating that the antigenic epitopes of Ova were conserved.

This data indicate that the primary structure of Ova was not altered by encapsulation and release from the CPTEG-containing polymers. Encapsulation and release from 50:50 CPH:SA microspheres also appeared to preserve antigenic epitopes of the 45 kDa Ova, however, only faint bands for the aggregated forms of Ova were detectable. Poly(SA) and 20:80 CPH:SA appeared to degrade Ova below the limit of detection by immunoblot analysis; also showed a similar effect. Even though equivalent amounts of protein were loaded on to each SDS-PAGE gel, the data indicated that polyclonal antibody was unable to detect Ova that had been encapsulated into poly(SA) and 20:80 CPH:SA copolymer, indicating that the protein had been degraded.

Based on the immunoblot analysis, there was less degradation of Ova that was encapsulated into the 50:50 CPH:SA microspheres and the antigenic recognition was similar to that of un-encapsulated Ova. It is likely that the observed degradation was related to the acidic microenvironment resulting from the degradation of poly(SA) and 20:80 CPH:SA. On the other hand, epitope integrity was better maintained in CPTEG-containing microspheres regardless of composition or fabrication method. This is likely due to the amphiphilic nature of the CPTEG-containing copolymers and the lower acidity of the resultant degradation products as previously reported.

Example 6

Model System for Treatment of Human Tuberculosis Infections

A new tractable system to model human tuberculosis (TB) infections has been developed. This system uses the small laboratory fish, Japanese medaka (*Oryzias latipes*), as the host and employs *Mycobacterium marinum* as the pathogen. Both pathogen and host genomes have been sequenced and are genetically tractable. Unlike *M. tuberculosis*, this surrogate pathogen can be easily manipulated, has good molecular genetic systems, grows fast and represents negligible BSL2 risks to laboratory workers.

Analogous to human TB, it was discovered that *M. marinum* mounts a life-long chronic disease in medaka without obvious overt symptoms in most individuals. Histopathology analysis revealed that target organs including the spleen, kidney and liver were infected, and granulomas were present in these tissues, the hallmark lesions of human TB. Mutant strains of *M. marinum* have been successfully engineered with inactivated genes that are either known or suspected to be virulence genes in *M. tuberculosis*. Reduced colonization and spread was observed for some of *M. marinum* mutants in fish. Detailed analyses of these and other mutants can be extended by performing infections with lines of medaka that are devoid of pigments.

To better model "fish TB" and monitor bacterial colonization, a mutant colony of medaka was established that is devoid of most pigments. These translucent lines of fish, referred to as "See Through Medaka (ST)", permit the viewing of all major organs in live animals (Broussard and Ennis, 2007). The ST fish were experimentally infected with wild-type *M. marinum* expressing either green fluorescent protein (gfp) or red fluorescent proteins (rfp). Real-time bacterial spread and colonization of organs by either gfp- or rfp-expressing bacteria were monitored in real time.

Bacterial colonization levels of target organs are conveniently correlated by fluorescent levels in living ST fish. Some sites of infections were uncovered in the ST fish were initially missed with classical histology, such as in the peritoneal lining, pancreas, fat and swim bladders. These unexpected sites of infections may be the long sought-after hideouts for latent bacteria. For human TB, all but a small subpopulation of the infectious load is killed by conventional antibiotic treatments. These hidden niches are thought to offer micro-environments where the latent "persisters" are all but refractory to killing by antibiotics.

For eradication this small but persistent subpopulation requires a six month treatment of a cocktail of three antibiotics. Failure to eradicate the persisters can lead to a relapse of TB, because bacteria eventually circulate from these infectious reservoirs and then reinoculate and those tissues where bacteria were successfully treated by antibiotics. Chronically infected ST fish were treated with two established anti-TB drugs, isoniazid and rifampin. These treatments provide insights into the anatomical locations where persistent *M. marinum* subpopulations reside. The regions of ST fish where the susceptible fluorescent bacteria are effectively killed by antibiotic treatment (i.e., "lights-out") were carefully monitored.

Tissues are being identified where fluorescent bacteria persist ("lights-on") despite antibiotic treatments. In situ imaging of these "lights-on" subpopulations can document the locations of these persistent reservoirs of bacteria. Directly monitoring the subpopulations residing in each infected tissue can allow for simultaneously evaluation of the relative efficacy of different anti-TB drugs in all of the infected tissues. Monitoring the response of the lights-on subpopulations to different antibiotics allows for discovering drugs that can efficiently target latent persisters.

The techniques described above allow for the investigation of whether chronic infections by either *Brucella* or *Mycobacterium* increase cancer risk to the host due to increased mutational loads in and around infected tissues. Human epidemiological studies have long correlated greater cancer risk for populations with chronic infectious diseases. For example, increased human risk has been best established for stomach cancer and chronic *Helicobacter pylori* infections also increased bladder/colon cancer and chronic Shistosomal infections. Increases in lung cancer has also been correlated with long-term TB patients. The increased risk of cancer is believed to stem from persistent, self-inflicted "bystander" DNA damage to host tissues from mutagens generated by phagocytes, like macrophages as well as other components of the immune system.

This connection between chronic inflammation associated with *Brucella* or *Mycobacterium* infections and increased cancer risk can be assessed by the techniques described above. Studies have found that chronic *Mycobacterium marinum* infections yielded approximately a five-fold increase in hepatocarcinoma frequency in medaka. These studies are being extended in medaka by testing the effects of variables such as, diet, stress and anti-inflammatory drugs that might influence cancer risks of chronically-infected animals. These studies are also being used to investigate the effects of known host tumor suppressors, DNA repair activities and error-prone DNA polymerases on mycobacterial-induced cancers. Colonies of fish carrying defined genetic mutations are being established in the following repair functions: p53, REV1 and RIC1. These mutant animals will be infected with *M. marinum* and the effects on hepatocarcinoma will be evaluated.

Example 7

Influences of Polymer Chemistry on Monocytic Uptake of Nanospheres

Polyanhydride copolymer chemistry (polymer structural composition and properties) affects the uptake and intracellular compartmentalization of nanospheres by THP-1 human monocytic cells. Polyanhydride nanospheres were prepared by an anti-solvent nanoprecipitation technique, as described in the examples above. Morphology and particle diameter were confirmed via scanning election microscopy and quasi-elastic light scattering, respectively. The effects of varying polymer chemistry on nanosphere and fluorescently labeled protein uptake by THP-1 cells were monitored by laser scanning confocal microscopy.

Polyanhydride nanoparticles composed of poly(sebacic anhydride) (SA), and 20:80 and 50:50 copolymers of 1,6-bis-(p-carboxyphenoxy)hexane (CPH) anhydride and SA were fabricated with similar spherical morphology and particle diameter (200 to 800 nm). Exposure of the nanospheres to THP-1 monocytes showed that poly(SA) and 20:80 CPH:SA nanospheres were readily internalized whereas 50:50 CPH:SA nanospheres had limited uptake. The chemistries also differentially enhanced the uptake of a red fluorescent protein-labeled antigen.

Accordingly, nanosphere and antigen uptake by monocytes can be directly correlated to the chemistry of the nanosphere. These results demonstrate the importance of choosing polyanhydride chemistries that facilitate enhanced interactions with bacterial infections and/or antigen presenting cells that are necessary in the initiation of efficacious immune responses.

Bioerodible polymers have been studied as sustainable drug delivery vehicles for over thirty years (1). Polyesters and polyanhydrides are two families of polymers that are strong candidates for biomedical applications because of the biocompatibility and bioresorbability of their degradation products (2). While polyesters, like poly(lactic-co-glycolic acid) (PLGA), have been approved by the FDA for many in vivo applications (3), their suitability for use as drug or vaccine delivery vehicles and disease treatment is affected by various factors that negatively impact the stability of encapsulated proteins. Research has shown that the bulk-erodible polyester-based delivery systems display rapid release profiles (4,5), produce low pH microenvironments (6-8), and can initiate moisture-induced protein aggregation (8-10).

In contrast, polyanhydrides are characterized by chemistry-dependent surface erosion and payload release (11-13), moderate pH micro environments (8,14,15), and superior protein stabilization capabilities (10,16,17). Polyanhydrides have been used to deliver plasmid DNA (18), proteins (9,13, 17), small molecular weight drugs (11,19,20), and vaccine immunogens (21,22). Alterations of polyanhydride chemistry modulate degradation rates from weeks to years, which can be exploited to best fit therapeutic needs (9,11,16). In addition, polyanhydride microspheres used as vaccine delivery vehicles exhibit a chemistry-dependent, immunomodulatory adjuvant effect (22). Kipper et al. showed that encapsulating tetanus toxoid (TT) into polyanhydride microspheres or co-delivering free TT along with the microspheres enhanced antigen-specific immune responses (22). Furthermore, the relative increase of polymer hydrophobicity effectively modulated the immune response from a dominant $T_H2$ (humoral) to a $T_H0$ (balanced) response. Together, these results indicate that polyanhydride microspheres are promising vehicles for vaccine delivery.

The polyanhydride chemistries used in the present study includes examples such as copolymers of sebacic anhydride (SA) and 1,6-bis(p-carboxyphenoxy)hexane (CPH) anhydride. With aromatic rings, the CPH unit is more hydrophobic than the aliphatic SA unit. Copolymers containing higher compositions of CPH have been shown to degrade slower than copolymers containing higher compositions of SA (9).

In the last several decades, the in vivo applications utilizing polymer carriers have transitioned from the use of large, implanted pellets (~1 mm) to microspheres (~5-20 µm) and, more recently, to nanospheres (~100-500 nm) (1,11). In comparison to implants, microspheres (or nanospheres) do not require surgical insertion or removal (22), can carry multiple drugs (20,23), and are phagocytosed by antigen presenting cells (APCs) (24). Inhalation and intranasal delivery can be realized with particles that are small enough to pass through the finely porous networks of the nasal, tracheal, and pulmonary filtration systems (25,26). In addition, multiple studies have shown that polymeric nanoparticles gain ready access into sub-mucosal layers of the nasal-associated and gut-associated lymphoid tissues much more effectively than microparticles (27-29). In comparison to microspheres, nanospheres were more readily taken up by APCs (30). Collectively, these characteristics underpin the functional diversity and enhanced capabilities of polyanhydride nanospheres.

For polyanhydride nanospheres to function as efficacious antimicrobial drug delivery devices and vaccine adjuvants, they must possess the ability to deliver the antimicrobial agent into the microbes, and to stimulate and to deliver antigen to APCs, respectively. In the present study, confocal microscopy was used to monitor both intracellular and extracellular interactions between polyanhydride nanospheres and APCs (31). In addition, confocal microscopy allowed for monitoring the ability of polyanhydride nanospheres to deliver antigens or antimicrobial agents via the endocytic pathway by evaluating the co-localization of polyanhydride nanospheres within specific sub-cellular compartments associated with antigen processing and presentation and pathogenic infection sites. Data demonstrate that systematically varying the chemistry of polyanhydride nanospheres (by varying the SA content in a CPH:SA copolymer) significantly affects nanosphere uptake by human monocytic cells. In addition, it was demonstrated that polymer chemistry significantly influences the uptake of a model antigen (Eα tagged with red fluorescent protein (RFP), henceforth referred to as Eα-RFP) by human monocytic cells.

Preparation of SA and CPH pre-polymers, copolymers, and nanospheres was carried out, for example, as described in Example 1.

Culture of THP-1 Human Monocytes and Co-Incubation with Nanospheres.

Tissue culture and subsequent derivation of adherent THP-1 monocytes was performed according to published reports (34) with some modification (35). Briefly, THP-1 cells were grown in suspension using RPMI 1640 growth medium supplemented with 10% newborn calf serum, 10 mM Glutamax, 25 mM HEPES, and 10 µ/mL penicillin-streptomycin antibiotics (complete RPMI). Adherent monocytes were derived from suspension cultures by stimulating cells with 5 nM phorbol-12-myristic-13-acetate (PMA) in 24 well tissue culture plates containing 10 mm glass coverslips inside each well at a final density of $5 \times 10^5$ cells per well. Following 24 hours PMA incubation, cultures were washed with PBS and incubated in fresh RPMI without PMA for 24 hours before nanospheres were added.

Polyanhydride nanospheres (in the form of dry powder) of poly(SA), 20:80 CPH:SA, or 50:50 CPH:SA were weighed and added to PBS (pH 7.4) at a stock concentration of 10 mg/mL. The nanospheres were briefly sonicated on ice for a total process time of 1 minute alternating 10 seconds pulse ON, 15 seconds Pulse OFF. Nanospheres (100 µg) were added to cell culture medium (0.5 ml/well), briefly mixed by pipetting before cultures were returned to the incubator (37° C., 5% $CO_2$). To evaluate phagocytic processes, the nanospheres were co-incubated with the THP-1 cells for 30 minutes. Cultures were washed and the cells were placed back in the incubator for 2 hours prior to analysis. To evaluate endocytic processes, the nanospheres were co-incubated with the THP-1 cells for 6 hours. Cultures were washed and the cells were placed back in the incubator for 48 hours prior to analysis.

Fluorescence Microscopy Techniques.

To observe time-dependent interactions of individual monocytes with nanospheres, cell monolayers incubated with nanospheres at indicated times were fixed with 4% paraformaldehyde (PFA) for 10 minutes at room temperature, and then washed with PBS. Acidic vesicles and lipid rafts in cell monolayers were labeled by incubating cells for 20 minutes prior to fixation with either Lysotracker at 1/2,000 dilution (DND-99)(acidic vesicles) or Alexa555 conjugated Cholera Toxin β-subunit (CTx) at 1/150 dilution (lipid rafts) (Molecular Probes-Invitrogen, Carlsbad, Calif.). Intracellular structures were immunofluorescently stained by incubating fixed coverslips with primary and secondary antibodies in PBS containing albumin and 0.1% saponin (BSP) (35). Stained coverslips were washed and mounted on glass slides (Pro-Long w/ Dapi; Molecular Probes-Invitrogen).

Epifluorescence and immunofluorescence microscopy was performed using either an Olympus IX-61 inverted microscope equipped with blue, green, and red filter sets with a cooled CCD camera or by an inverted Leica NTS laser scanning confocal microscopy (LSCM). The LSCM was equipped with ApoChromatic x63 oil and x100 oil objectives and UV, Argon, Krypton and HeNe laser lines equipped with three photomultiplier detection tubes. Optimal step size for Z-stack image data was determined empirically from pilot studies to be 0.3 μm. Co-localization analysis, relative nanosphere uptake comparisons, and final images were prepared using Image J v1.36b image analysis software loaded with particle counting algorithms (36).

Eα-RFP Antigen Preparation and Cellular Internalization by Monocytes.

The IPTG inducible Eα-RFP expression construct (37) was introduced into *Escherichia coli* DH5α by heat shock followed by selecting 50 mg/mL ampicillin-resistant colonies. Broth cultures of transformed bacteria were induced by the addition of IPTG to overnight cultures. Crude cell lysates prepared using the Novagen Bugbuster extraction reagent (Gibbstown, N.J.) were passed through a Profinity IMAC Ni-charged resin (BioRad; Hercules, Calif.). Imidazole eluted Eα-RFP protein was dialyzed overnight at 4° C. and final preparations were shown to be free of detectable LPS contamination by the limulus ameobocyte lysate (LAL) assay (Cambrex; Walkersville, Md., USA). Fluorescence signal intensity of internalized protein was detected using standard epi-fluorescence microscopy employing TRITC/rhodamine filter set with 510-560 nm excitation and 575-645 emission. Image black levels for the RFP protein were set using cells not incubated with RFP. Exposure times for RFP detection were kept constant throughout the experimental groups to facilitate accurate comparative analysis. Bar graphs of the relative pixel intensity of internalized RFP were calculated from RAW-RFP images using the ImageJ/plugin/histogram function. These bar graphs reveal the relative pixel intensity of the RFP protein detected in the presence and absence of nanospheres.

Nanosphere Characterization.

Figure 10:
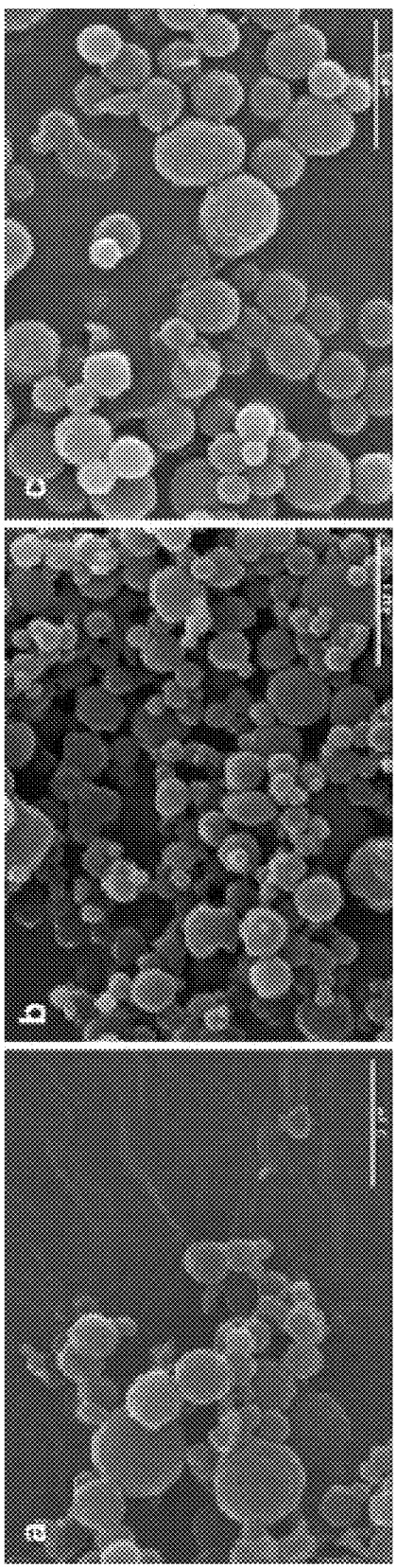
FIG. 10 illustrates scanning electron photomicrographs of a. poly(SA) nanospheres; b. 20:80 CPH:SA nanospheres; and c. 50:50 CPH:SA nanospheres. Scale bars=2 µm.

Scanning electron photomicrographs of the FITC-dextran loaded nanospheres of varying formulations are presented in FIG. 10. The photomicrographs show that the nanoparticles are spherical, and while there are some small variations, the nanospheres appear to be relatively uniform in size and shape. Light scattering size distribution data show nanosphere diameters for all polymers fall between 200 and 800 nm.

Each batch of nanospheres was analyzed by light scattering and particle size was measured using duplicate samples. For each polymer chemistry, the data from three different lots of nanospheres were analyzed in this manner and the compiled data are shown in Table I. The standard deviations were determined for the overall accumulated size distribution data for each polymer.

TABLE I

Particle Size Data Compiled from Light Scattering Measurements (n = 3).

| Polymer | Average Particle Diameter (nm) |
| --- | --- |
| poly SA | 283 ± 45 |
| 20:80 CPH:SA | 348 ± 48 |
| 50:50 CPH:SA | 397 ± 121 |

Data reported as mean ± SD.

Analysis shows that there is no statistically significant difference in average particle size among the different polymer formulations (p=0.13). This data demonstrates that polyanhydride nanospheres fabricated by the PAN method can be reproducibly prepared with similar morphology and particle diameters regardless of copolymer chemistry. Having particles of similar size is important in limiting the variables that are introduced into in vitro and in vivo experiments, especially when evaluating a polymer chemistry effect. While not statistically significant, there was a slight trend for a positive correlation between particle size and CPH content.

The thermodynamic and kinetic balance between nucleation and growth dictates the resulting average particle size. The soluble material must nucleate particles and then more material can either precipitate on the surface of these already formed particles or new particles can be nucleated (38). Copolymers with a higher SA content are less hydrophobic and more non-polar than those with a higher CPH content. When precipitating from a polar solvent into an aliphatic antisolvent bath, copolymers with a higher SA content may more easily nucleate new particles. If nucleation is favored, it would cause more particles to be formed with a smaller average particle size.

Cellular Interactions of Nanospheres with Human Monocytes.

To determine whether polymer chemistry affects nanoparticle internalization and intracellular deposition within APCs, adherent human THP-1 monocytes were incubated separately with poly(SA), 20:80 CPH:SA, or 50:50 CPH:SA nanospheres. LSCM was utilized to evaluate and compare the interactions of nanospheres with cells and their eventual intracellular localization.

Internalization.

Figure 11:
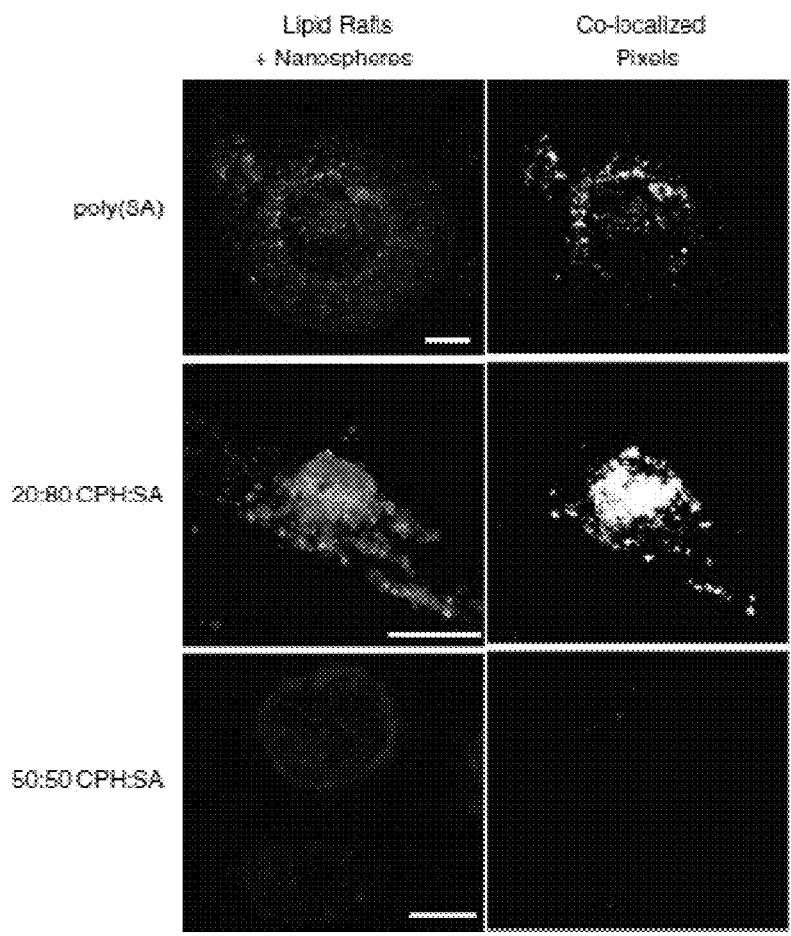
FIG. 11 illustrates confocal photomicrographs of FITC-labeled polyanhydride nanospheres internalized by THP-1 cells. Adherent monocytes were incubated with nanospheres for 30 minutes before cultures were washed and continued to incubate for an additional 2 hours. Poly(SA) and 20:80 CPH:SA nanoparticles were internalized to a much greater extent than 50:50 CPH:SA nanospheres. The majority of internalized poly(SA) and 20:80 CPH:SA were bound by cholesterol rich membranes as indicated by the high degree of co-localization. Representative images were captured by LSCM. Lipid rafts were identified using Alexa 555 CTx (Molecular Probes). Scale bar=5 µm.

Nanospheres introduced into cell culture medium did not form large aggregates and remained uniformly dispersed prior to settling at the bottom of the tissue culture well during co-incubation with the THP-1 cells. The nanospheres were then rapidly internalized by THP-1 monocytes via cellular events consistent with phagocytosis (FIG. 11). Observations supporting this conclusion include centrifugation-independent internalization, temperature-dependent internalization, and internalization in the absence of an overabundance of extracellular particles.

Confocal photomicrographs in FIG. 11 depict monocytes that have internalized nanospheres and values presented in Table II indicate the percentage of THP-1 cells per field of view that have cell associated nanospheres at 2 or 48 hours post exposure. Cells were imaged at 1000× total magnification and the average number of cells in each Field of View (FOV) was 25. FOVs were randomly selected and the numbers of THP-1 cells with FITC-loaded polyanhydride nanospheres or without nanospheres were recorded. The percentages and standard deviations of THP-1 cells positive for nanospheres were calculated from values for ≧5 FOV images for each nanosphere chemistry and time point (cells with FITC-nanospheres/total # cells scored). The total cells scored positively for clear association with FITC nanospheres were combined from data collected over three to five independent experiments.

TABLE II

Association of Polyanhydride Nanospheres with THP-1 Cells Varies Depending on Polymer Chemistry.

| Polymer | Percent monocytes with internalized nanospheres[a] | |
|---|---|---|
| | 2 h (phagocytosis) | 48 h (phagocytosis and endocytosis) |
| Poly(SA) | 87.9% ± 17.1% | 96.3% ± 11.7% |
| 20:80 CPH:SA | 27.1% ± 14.8% | 91.2% ± 22.2% |
| 50:50 CPH:SA | 8.1% ± 10.6% | 53.1% ± 28.3 |

[a]Average percent nanospheres positive monocytes calculated per x 100 field of view image.

The data in Table II indicate that in the experiments designed to evaluate phagocytosis where the exposure to nanospheres was 30 minutes, the least hydrophobic polymers (i.e., poly(SA)) were more rapidly internalized than the more hydrophobic (i.e., CPH-containing) polymers (FIG. 11). In contrast, the 48 hours co-localization experiments employ a longer exposure time of nanospheres with cells lasting 6 hours. In these experiments, where endocytosis plus the initial phagocytosis would contribute to total nanosphere uptake, it was observed that ~96% of the THP-1 cells contained poly(SA) nanospheres, while the uptake of 20:80 CPHSA and 50:50 CPH:SA was ~91% and ~53%, respectively. These results indicate that the polymer chemistry of the polyanhydride nanospheres affects the uptake efficiency of these nanospheres by monocytes.

Unlike CPH-containing nanospheres, poly(SA) nanospheres were more efficiently internalized by phagocytic processes (30 minutes exposure to cells) and did not require the extended time (6 hours) associated with endocytic processes. The more hydrophobic nanospheres (i.e., CPH-rich) were not internalized by phagocytic pathways (~8%). However, with time, all the formulations were internalized; but, 50:50 CPH:SA nanospheres were internalized to a lesser extent (~53%, Table II). Overall, monocyte uptake of polyanhydride nanospheres correlated with decreasing hydrophobicity (poly(SA)>20:80 CPHSA>50:50 CPHSA).

The degree of hydrophobicity is a significant factor influencing nanosphere uptake. The hydrophobic nature of these particles can facilitate their interaction with hydrophobic lipid-rich micro-domains in the cell membrane, including lipid rafts. Lipid rafts contain many membrane-bound cofactors that comprise receptor complexes, such as receptors for complement, antibodies, and serum and extracellular matrix proteins (39-41). In contrast with phagocytosis, increasing polymer hydrophobicity can facilitate closer nanosphere-to-cell interactions and increase the probability of internalization through constitutive endocytic or macropinocytotic pathways. These hydrophobic interactions facilitate nanosphere internalization by direct association with surface receptors or through direct interactions with the plasma membrane.

Pattern recognition receptors (PRRs) are another key receptor type found in lipid rafts of APCs. PRRs recognize pathogen-associated molecular patterns (PAMPs), which are repetitive patterns of molecular structure found in both microorganisms and the mammalian host. Examples of PAMPs include lipopolysaccharide and flagellin from bacteria as well as hyaluronan and uric acid from mammals. All of these PAMPs signal "danger" to the host, be it in the context of infection or cellular damage. Hydrophobic characteristics have been ascribed to many PAMPs and are thought to be partly responsible for their immunostimulatory properties (42). In the context of the polyanhydride co-polymers, surface patterns of intervening hydrophobic moieties (e.g., CPH and SA) may mimic PAMPs, facilitate interactions with PRRs present on the surface of APCs and subsequently enhance the ability of APCs to activate T cells (43, 44). Internalization and co-localization of antigen-loaded nanospheres within the endocytic pathway may, in part, explain the adjuvanticity of polyanhydride nanospheres (22).

Intracellular Localization.

Figure 12:
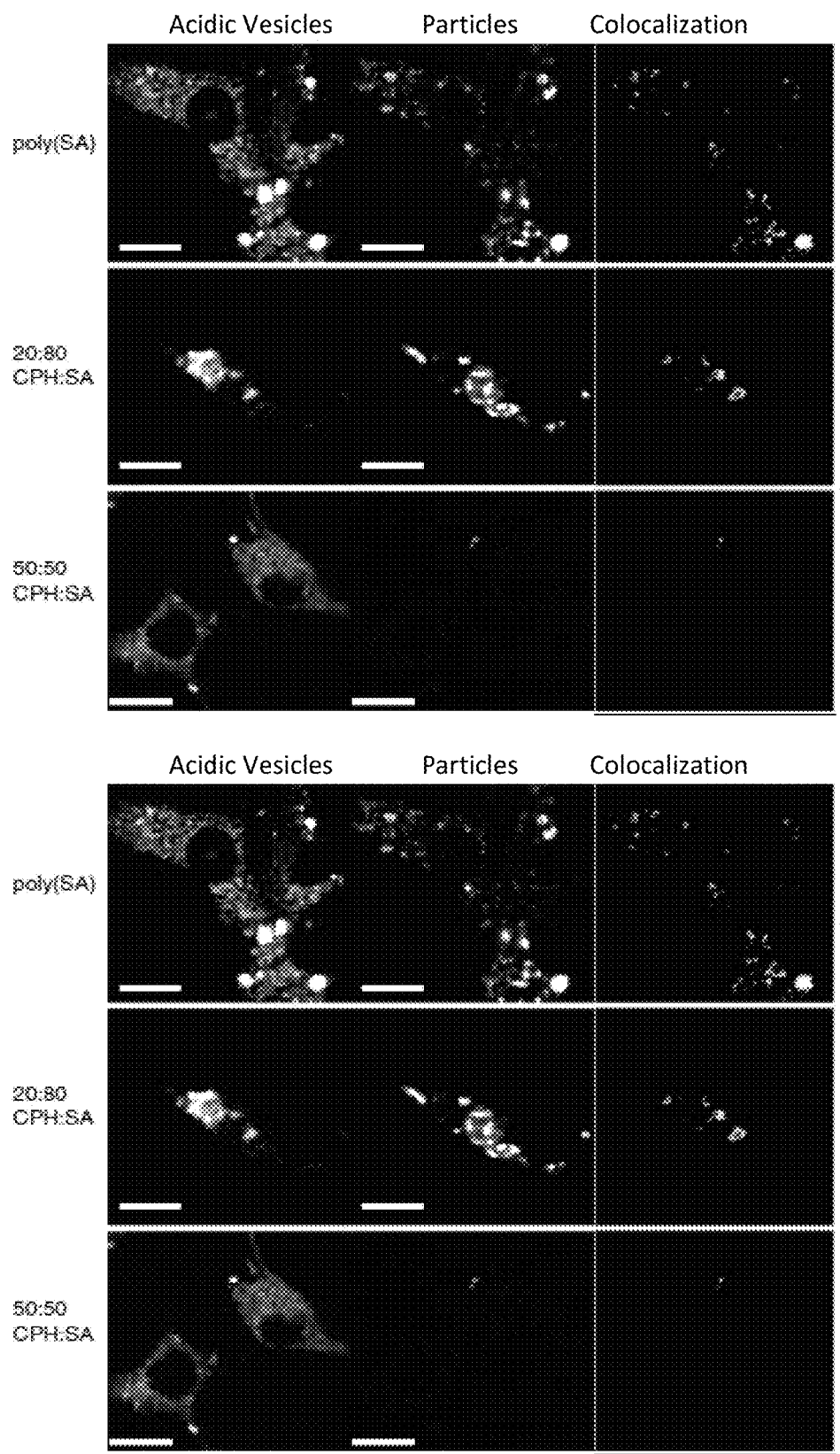
FIG. 12 illustrates confocal images of the intracellular localization of FITC-nanospheres in THP-1 cells 48 h after uptake. Representative images were captured by LSCM and processed using ImageJ. The majority of internalized poly (SA) and 20:80 CPH:SA nanospheres were bound by cholesterol rich membranes as indicated by the high degree of co-localization. Acidic vesicles (two left columns) were identified using the pH responsive Lysotracker dye and cholesterol rich lipid rafts (two right columns) were visualized using Alexa 555 conjugated CTx (Molecular Probes). Note the general absence of FITC 50:50 CPH:SA nanospheres compared to 20:80 CPH:SA and poly(SA). Scale bar=5 µm.
Figure 15:
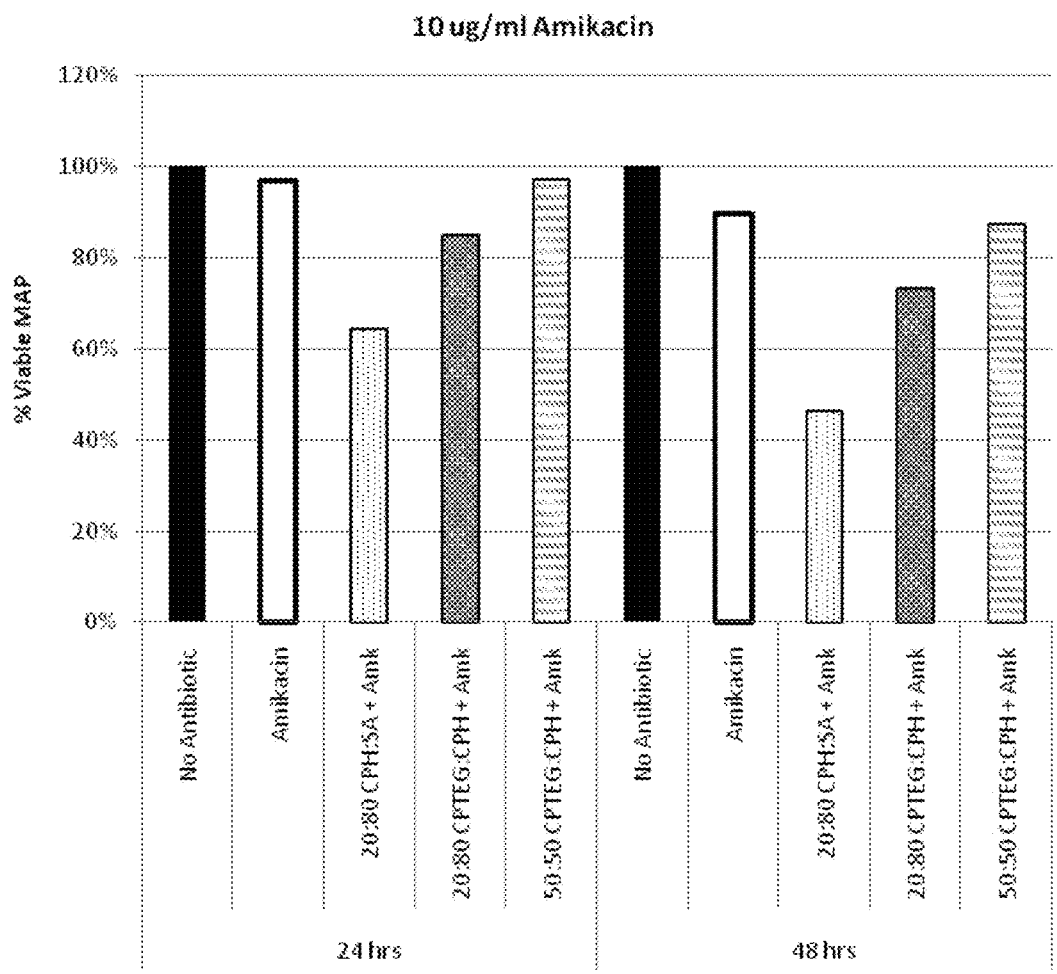
FIG. 15 illustrates viability of *Mycobacterium avium* subsp. *paratuberculosis* (MAP) at 24 hours and 48 hours after treatment with PBS solubilized amikacin or polyanhydride particles containing 10 µg/mL mg amikacin.
Figure 16:
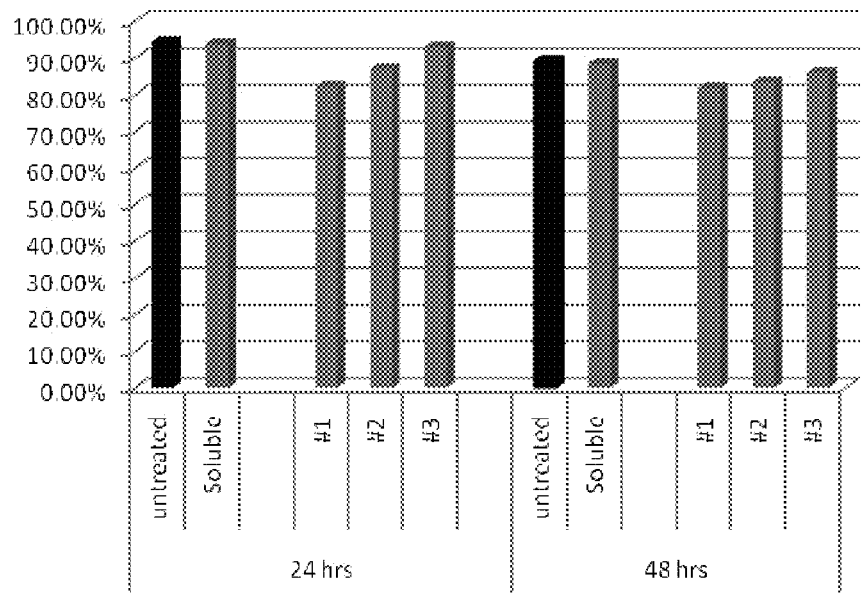
FIG. 16 illustrates viability of MAP in broth at 24 hours and 48 hours after treatment with PBS solubilized amikacin or polyanhydride particles containing 1.25 µg/mL amikacin.
Figure 17:
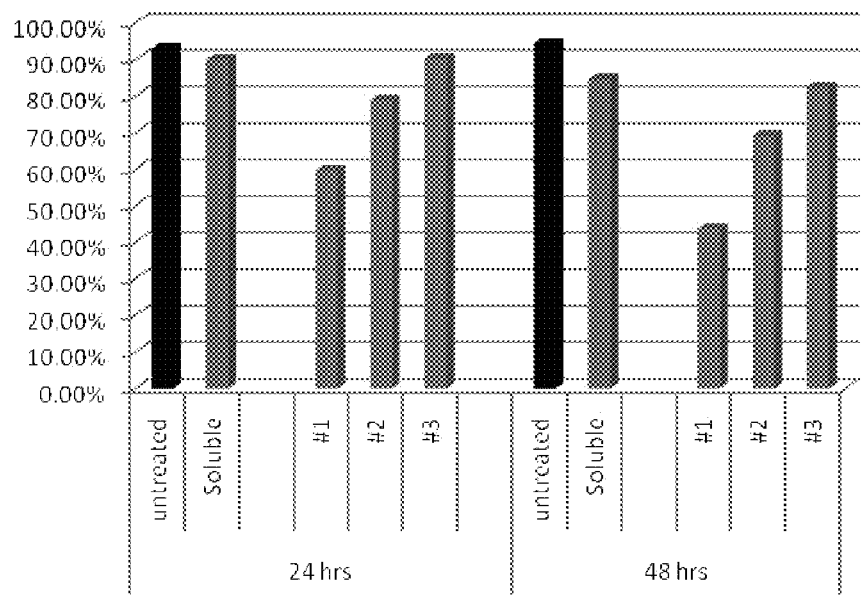
FIG. 17 illustrates viability of MAP in broth at 24 hours and 48 hours after treatment with PBS solubilized amikacin or polyanhydride particles containing 10 µg/mL amikacin.
Figure 18:
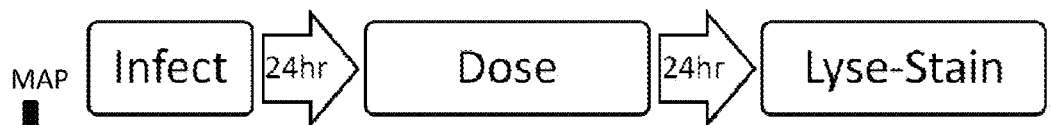
FIG. 18 illustrates a schematic showing how determinations of intracellular bacterial viability and extracellular bacterial killing were obtained in Example 9, according to various embodiments.
Figure 18:
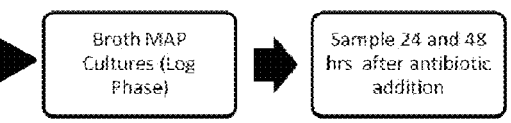
Figure 19:
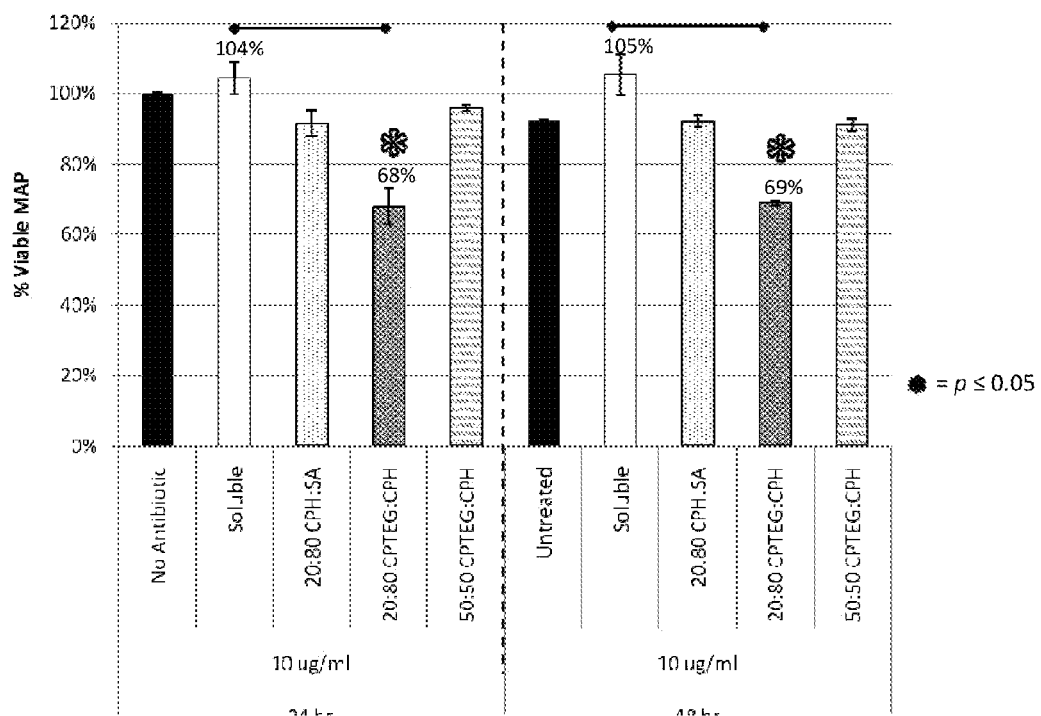
FIG. 19 illustrates percent viability of intracellular MAP in U937 human pro-monocytes at 24 hours and 48 hours after treatment with PBS solubilized amikacin or polyanhydride particles containing 10 µg/mL amikacin.
Figure 20:
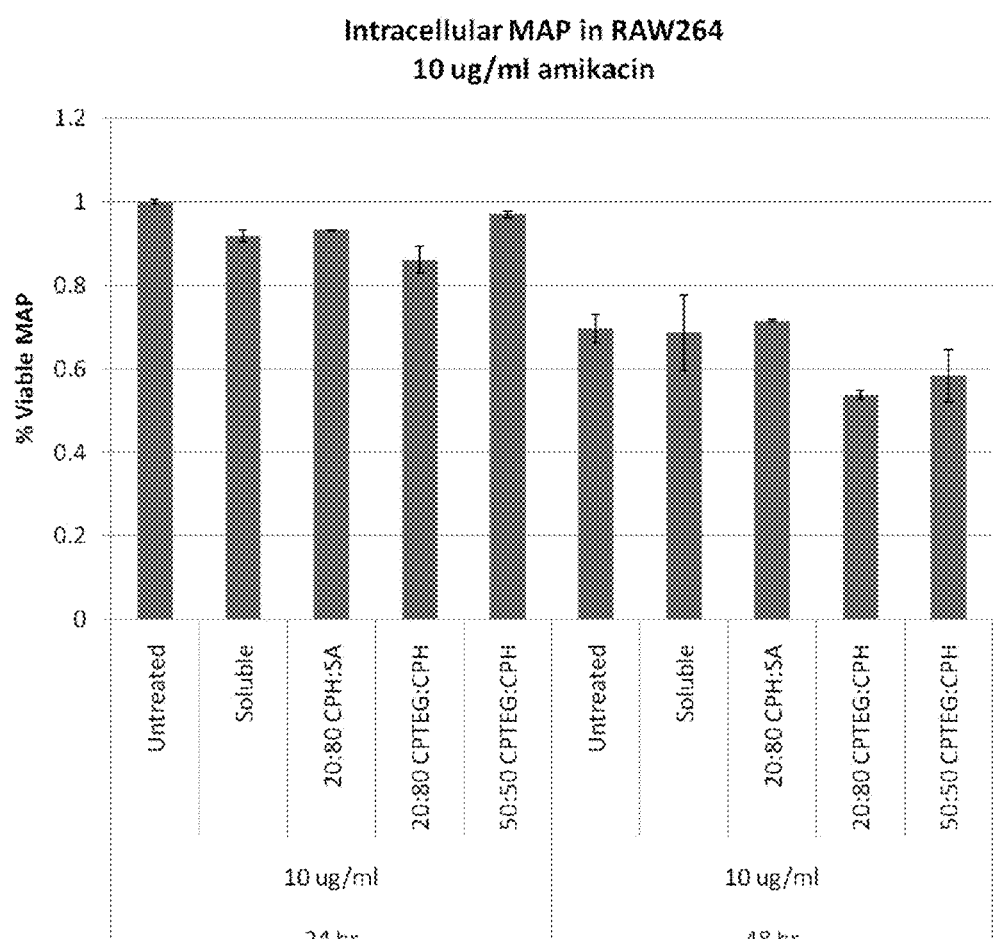
FIG. 20 illustrates percent viability of intracellular MAP in RAW264 at 24 hours and 48 hours after treatment with PBS solubilized amikacin or polyanhydride particles containing 10 µg/mL amikacin.
Figure 21:
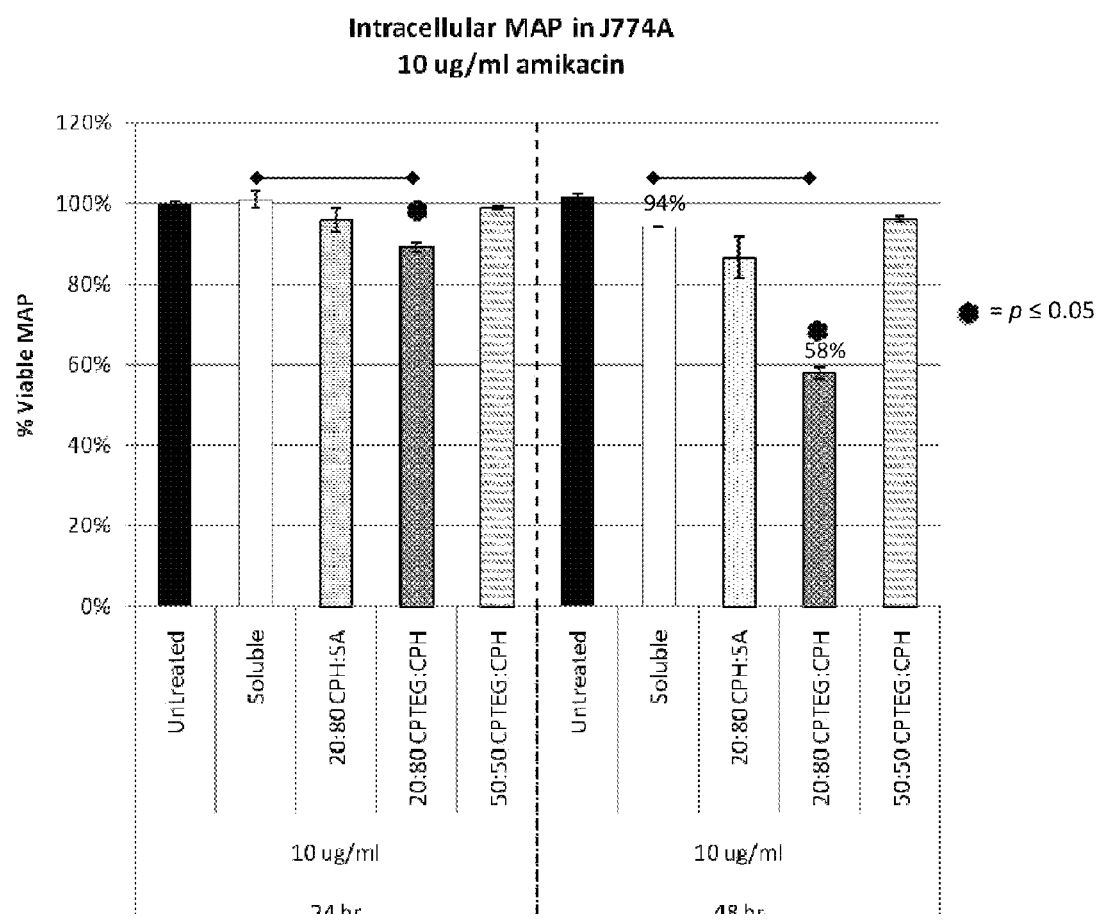
FIG. 21 illustrates percent viability of intracellular MAP in J774A at 24 hours and 48 hours after treatment with PBS solubilized amikacin or polyanhydride particles containing 10 µg/mL amikacin.

In general, intracellular degradation and processing of exogenously presented antigen occurs when lysosomes fuse with late endosomes containing antigen. In contrast, endogenous antigen is processed within the cytosol by the proteosome (45). As a result, antigen fate (i.e., MHC I vs MHC II presentation) is largely decided by intracellular location. Given the variable surface chemistry presented by the different polyanhydrides, the intracellular distribution of nanospheres 48 hours after uptake was analyzed. The majority of particles were found to be intact and located within membrane bound vesicles that were characterized as acidic and CTx+ (FIG. 12). In color versions of these photomicrographs, the FITC-dextran containing nanospheres appear green, the acidic vesicles are red (Lysotracker), and co-localized nanospheres within acidic vesicles appear yellow. The data and images clearly indicate that the polyanhydride chemistries studied resulted in localization of the nanospheres into the acidic phagolysosomal compartments of the cells.

The majority of these particles were rapidly targeted to the endosomal pathway, and localized within vesicles exhibiting staining characteristics and morphology consistent with MHC class II loading compartments (46). At 48 hours, ~10% of the poly(SA) and 20:80 CPH:SA nanospheres did not appear to be located within acidic or lipid raft containing vesicles (FIG. 11). A lack of localization within either of these major intracellular compartments is consistent with nanospheres that are free within the cellular cytosol. Release of antigen from nanospheres located within the cellular cytosol would be processed and directed to the MHC class I presentation pathway (45). However, the data presented in FIGS. 11 and 12 indicate various amounts of nanospheres can reach the cytosol.

Antigen Internalization.

As previously discussed, polyanhydride nanospheres serve as antigen delivery platforms to APCs. Nanosphere-encapsulated immunogens can be released intracellularly following internalization and slow polymer degradation (8). However, some nanospheres may release antigen prior to uptake, providing a source of soluble antigen delivered to APCs via endocytosis. To evaluate the ability of nanospheres to stimulate soluble antigen internalization by APCs, the THP-1 cells were co-incubated with blank nanospheres (poly (SA), 20:80 CPH:SA, or 50:50 CPH:SA) and soluble Eα-RFP (37), fixed, and visualized by epifluorescence microscopy. Representative photomicrographs and bar graphs summarizing cell associated RFP data are provided in FIG. 9.

Comparisons among the three chemistries reveal that after 2 hours of co-incubation, all three chemistries dramatically increased the amount of soluble antigen internalized by monocytes. A potential mechanism for the increase in uptake stimulated by the nanospheres is that the protein itself is able to adsorb on the surface of nanospheres that are then subsequently internalized by the APC. However, preliminary experiments failed to detect soluble RFP adsorbing onto FITC-labeled nanospheres and culture conditions include ample amounts of serum proteins present in the 10% fetal bovine serum supplemented medium. Moreover, the dramatic increase in the uptake of soluble RFP was also detected for 50:50 CPH:SA even though these particles serve as poor targets for uptake themselves (Table II, FIGS. 11 and 12). This data demonstrates that the polymer chemistry of the polyanhydride nanospheres influences the ability of APCs to internalize soluble antigen.

Accordingly, the unique cellular interactions elicited by polyanhydride nanospheres are a function of the particles' distinct physical and chemical properties that modulate the persistence and intracellular distribution of antigen. Polyanhydride nanospheres were internalized and distributed within human monocytes in a chemistry-dependent manner. Chemical structure of the polymers also influences the ability of nanospheres to enhance monocytic uptake of soluble antigen. Together, this data highlights the importance of chemistry in designing polyanhydride nanospheres as vaccine or drug delivery vehicles intended for specific applications and/or targeting desired intracellular locations. Thus, the drug encapsulated nanoparticles can be effectively used to deliver active agents to target cells to inhibit microbe growth and to deliver vaccines.

Example 7

Citations

1. I. Preis, and R. S. Langer. A single-step immunization by sustained antigen release. *J. Immunol. Methods.* 28(1-2): 193-197 (1979).
2. J. H. Wilson-Welder et al. Vaccine adjuvants: Current challenges and future approaches. *J. Pharm. Sci.* 2008.
3. S. P. Schwendeman. Recent advances in the stabilization of proteins encapsulated in injectable PLGA delivery systems. *Crit. Rev. Ther. Drug Carr. Syst.* 19:73-98 (2002).
4. A. Gopferich. Polymer bulk erosion. *Macromolecules.* 30:2598-2604 (1997).
5. Y. Wang et al. Controlled release of ethacrynic acid from poly (lactide-co-glycolide) films for glaucoma treatment. *Biomaterials.* 25(18):4279-4285 (2004).
6. K. Fu et al. Visual evidence of acidic environment within degrading poly(lactic-co-glycolic acid) (PLGA) microspheres. *Pharm. Res.* 17(1):100-106 (2000).
7. A. G. Ding, and S. P. Schwendeman. Acidic microclimate pH distribution in PLGA microspheres monitored by confocal laser scanning microscopy. *Pharm. Res.* 25(9):2041-2052 (2008).
8. A. S. Determan et al. Protein stability in the presence of polymer degradation products: consequences for controlled release formulations. *Biomaterials.* 27(17):3312-3320 (2006).
9. A. S. Determan et al. Encapsulation, stabilization, and release of BSA-FITC from polyanhydride microspheres. *J. Control. Release.* 100(1):97-109 (2004).
10. G. Zhu, S. R. Mallery, and S. P. Schwendeman. Stabilization of proteins encapsulated in injectable poly(lactic-co-glycolic acid). *Nat. Biotechnol.* 18:52-57 (2000).
11. M. J. Kipper et al. Design of an injectable system based on bioerodible polyanhydride microspheres for sustained drug delivery. *Biomaterials.* 23(22):4405-4412 (2002).
12. E. Shen et al. Mechanistic relationships between polymer microstructure and drug release kinetics in bioerodible polyanhydrides. *J. Control. Release.* 82(1):115-125 (2002).
13. E. Ron et al. Controlled release of polypeptides from polyanhydlides. *Proc. Natl. Acad. Sci. USA.* 90(9):4176-4180 (1993).
14. L. Shieh et al. Erosion of a new family of biodegradable polyanhydrides. *J. Biomed. Materi. Res.* 28(12):1465-1475 (1994).
15. J. P. Jain et al. Role of polyanhydrides as localized drug carriers. *J. Control. Release.* 103(3):541-563 (2005).
16. A. S. Determan et al. The role of microsphere fabrication methods on the stability and release kinetics of ovalbumin encapsulated in polyanhydride microspheres. *J. Microencapsul.* 23(8):832-843 (2006).
17. Y. Tabata, S. Gutta, and R. Langer. Controlled delivery systems for proteins using polyanhydride microspheres. *Pharm. Res.* 10(4):487-496 (1993).
18. B. A. Pfeifer et al. Poly(ester-anhydride):poly(beta-amino ester) microspheres and nanospheres: DNA encapsulation and cellular transfection. *Int. J. Pharm.* 304(1-2):210-219 (2005).
19. N. B. Shelke, and T. M. Aminabhavi. Synthesis and characterization of novel poly(sebacic anhydride-co-Pluronic F68/F127) biopolymeric microspheres for the con trolled release of nifedipine. *Int. J. Pharm.* 345(1-2):51-58 (2007).
20. W. Hsu et al. Local delivery of interleukin-2 and adriamycin is synergistic in the treatment of experimental malignant glioma. *J. Neurooncol.* 74(2):135-140 (2005).
21. J. Hanes, M. Chiba, and R. Langer. Degradation of porous poly (anhydride-co-imide) microspheres and implications for controlled macromolecule delivery. *Biomaterials.* 19(1-3):163-172 (1998).
22. M. J. Kipper et al. Single dose vaccine based on biodegradable polyanhydride microspheres can modulate immune response mechanism. *J. Biomed. Materi. Res. Part A.* 76(4):798-810 (2006).
23. C. Berkland et al. Microsphere size, precipitation kinetics and drug distribution control drug release from biodegradable polyanhydride microspheres. *J. Control. Release.* 94(1):129-141 (2004).
24. F. X. Lacasse et al. Influence of surface properties at biodegradable microsphere surfaces: effects on plasma protein adsorption and phagocytosis. *Pharm. Res.* 15(2): 312-317 (1998).
25. J. A. Schwab, and M. Zenkel. Filtration of particulates in the human nose. *Laryngoscope.* 108(1):120-124 (1998).
26. P. A. Jaques, and C. S. Kim. Measurement of total lung deposition of inhaled ultrafine particles in healthy men and women. *Inhal. Toxicol.* 12(8):715-731 (2000).
27. M. P. Desai et al. Gastrointestinal uptake of biodegradable microparticles: effect of particle size. *Pharm. Res.* 13(12): 1838-1845 (1996).
28. T. Jung et al. Tetanus toxoid loaded nanoparticles from sulfobutylated poly(vinyl alcohol)-gradt-poly(lactide-co-glycolide): evaluation of antibody response after oral and nasal application in mice. *Pharm. Res.* 18(3):352-360 (2001).
29. L. Illum. Nanoparticulate systems for nasal delivery of drugs: a real improvement over simple systems? *J. Pharm. Sci.* 96(3):473-483 (2007).
30. M. P. Desai et al. The mechanism of uptake of biodegradable microparticles in Caco-2 cells is size dependent. *Pharm. Res.* 14(11):1568-1573 (1997).
31. J. E. Fuller et al. Intracellular delivery of core-shell fluorescent silica nanoparticles. *Biomaterials.* 29(10):1526-1532 (2008).
32. A. Conix. Poly[1,3-bis(p-carboxyphenoxy)propane anhydride]. *Macromolecular Synthesis.* 2:95-98 (1966).
33. E. Mathiowitz et al. Biologically erodible microspheres as potential oral drug delivery systems. *Nature.* 386(6623): 410-414 (1997).

34. R. W. Stokes, and D. Doxsee. The receptor-mediated uptake, survival, replication, and drug sensitivity of *Mycobacterium tuberculosis* within the macrophage-like cell line THP-1: a comparison with human monocyte-derived macrophages. *Cell. Immunol.* 197(1):1-9 (1999).
35. B. H. Bellaire, R. M. Roop I I, and J. A. Cardelli. Opsonized virulent *Brucella abortus* replicates within nonacidic, endoplasmic reticulum-negative, LAMP-1-positive phagosomes in human monocytes. *Infecation and Immunity.* 73(6):3702-3713 (2005).
36. *ImageJ.* Image Processing and Analysis in Java [cited 2008 August 3rd); Available from: http://rsb.info.nih.gov/ij/.
37. A. A. Itano et al. Distinct dendritic cell populations sequentially present antigen to CD4 T cells and stimulate different aspects of cell-mediated immunity. *Immunity.* 19(1):47-57 (2003).
38. E. Mathiowitz, et al. Process for preparing microparticles through phase inversion phenomena. 2003: United States of America.
39. P. Lajoie, and I. R. Nabi. Regulation of raft-dependent endocytosis. *J. Cell. Mol. Med.* 11(4):644-653 (2007).
40. N. Gupta, and A. L. DeFranco. Visualizing lipid raft dynamics and early signaling events during antigen receptor-mediated Blymphocyte activation. *Mol. Biol. Cell.* 14(2):432-444 (2003).
41. Z. Wolf et al. Monocyte cholesterol homeostasis correlates with the presence of detergent resistant membrane microdomains. *Cytometry Part A.* 71(7):486-494 (2007).
42. S. Y. Seong, and P. Matzinger. Hydrophobicity: an ancient damage-associated molecular pattern that initiates innate immune responses. *Nat. Rev. Immunol.* 4(6):469-478 (2004).
43. M. G. Netea et al. From the Th1/Th2 paradigm towards a Toll-like receptor/T-helper bias. *Antimicrob. Agents Chemother.* 49(10):3991-3996 (2005).
44. P. Elamanchili et al. "Pathogen-mimicking" nanoparticles for vaccine delivery to dendritic cells. *J. Immunother.* 30(4):378-395 (2007).
45. A. L. Goldberg et al. The importance of the proteasome and subsequent proteolytic steps in the generation of antigenic peptides. *Mol. Immunol.* 39(3-4):147-164 (2002).
46. E. M. Hiltbold, and P. A. Roche. Trafficking of MHC class II molecules in the late secretory pathway. *Curr. Opin. Immunol.* 14(1):30-35 (2002).
Other citations that provide useful information include:
1. Lecaroz et al. Poly(D,L-lactide-coglycolide) particles containing gentamicin: pharmacokinetics and pharmacodynamics in *Brucella melitensis*-infected mice. Antimicrob. Agents Chemother. 2007, 51: 1185-1190.
2. Bellaire et al. The siderophore 2,3-dihydroxybenzoic acid is not required for virulence of *Brucella abortus* in BALB/c mice. Infect. Immun. 1999, 67: 2615-2618.
3. Baldwin and Parent. Fundamentals of host immune response against *Brucella abortus*: what the mouse model has revealed about control of infection. Vet. Microbiol. 2002, 90:367-382.
4. Bellaire B H, Roop R M, 2nd, Cardelli J A. Opsonized virulent *Brucella abortus* replicates within nonacidic, endoplasmic reticulum-negative, LAMP-1-positive phagosomes in human monocytes. Infect. Immun. 2005, 73: 3702-3713.
5. Rittig et al. Intracellular survival of *Brucella* spp. in human monocytes involves conventional uptake but special phagosomes. Infect Immun 2001, 69: 3995-4006.

Example 8

Polyanhydride Nanospheres Provide Improved Antibiotic Treatments

The polyanhydride nanospheres described herein demonstrated improved antibiotic activity of doxycycline and other antibiotics to kill intracellular, virulent *Brucella abortus* 2308 in human and mouse monocytes. The polyanhydride nanospheres also demonstrated sustained release with retained antimicrobial activity using disk diffusion assay against virulent *Brucella canis*. Increased antibiotic activity on bacteria in culture alone (not associated with infection) was observed. The increase was approximately 30× greater than soluble doxycycline alone. Thus, encapsulation of antibiotics could effectively treat a variety of bacteria, including Antibiotic Resistant Methacillin Resistant *Staphylococcus aureus* (MRSA), Extremely Drug Resistant *Mycobacterium tuberculosis* (XTBR), Gram positive bacteria such as *Streptococcus* and *Bacillus*, protozoans such as *Leishmania*, and enveloped viruses such as influenza and HIV. The particles were confirmed to be stable within dendritic cells and monocytes. Data indicated that the particles slowly degrade over more that 5 days with continued release of the cargo antimicrobial agents.

FIG. 13 illustrates the enhanced killing of intracellular *B. abortus* by analysis of a viability experiment at 72 hours post-inoculation, where 20:80 CPH:SA and 20:80 CPTEG:CPH polyanhydride particles with doxycycline cargo were significantly more effective at killing *B. abortus* than doxycycline solubilized in a PBS solution. The killing of intracellular *Brucella abortus* 2308 within human monocytes was enhanced through antibiotic encapsulation. Human monocytes cultures were infected with virulent *B. abortus* 2308 to establish a productive intracellular infection. At 24 hours, infected cultures were supplemented with 10 μg/mL of doxycycline in either soluble form (PBS solution) or encapsulated in PA polymers (vertical arrow in FIG. 13). Following an additional 48 hours of incubation (t=72 hours, total infection), non-treated and drug treated cultures were washed, and lysed to release intracellular bacteria, which were subsequently diluted serially and plated on solid agar medium.

The antimicrobial agent (e.g., doxycycline) was either solubilized in a PBS solution or used by preparing a slurry of PA particles in a PBS solution. The concentration (μg/mL) an antimicrobial agent was calculated by preparing PA particles with 5 wt. % antibiotic in the particles. Then a proportional amount of PA particles were added to a PBS buffer (e.g., 20× the mass of particle compared to the mass of antimicrobial agent directly dissolved in the PBS buffer).

FIG. 14 shows the continued antibiotic release by serial disc transfer of polyanhydride particles containing doxycycline. Antibiotic release from cellulose filter disks receiving soluble doxycycline or equivalent amounts of PA nanoparticle encapsulated doxycycline was analyzed. Liquid solutions of either soluble doxycycline or PA-encapsulated doxycycline were place onto filter paper to conduct standard zone of inhibition measurements on agar *Brucella canis* spread plates. After 24 hours of incubation, zones of inhibition were measured and the filter disks were aseptically removed and placed onto fresh *B. canis* spread plates to measure zones of inhibition following an additional 24 hours of incubation. Only PA nanoparticle encapsulated doxycycline filters retained any residual antibiotic activity following serial transfer. This experiment demonstrates the continued antibiotic release from degrading PA nanoparticles.

These data demonstrate steady and delayed release of antibiotic and that released antibiotic retains full antimicrobial activity and effectiveness against a human and animal pathogen Brucella canis. The disc treated with PA nanoparticles continued to provide zones of inhibition on fresh B. canis spread plates with full activity after 48 hours and additional activity at 72 hours. The antimicrobial activity of the particles can persist for several days, although the activity begins to decrease after 72 hours, whereas dissolved antibiotic alone displayed no activity on the disk after one plate treatment.

Particle internalization and stability at 48 hours post internalization by Murine Bone Marrow Derived Monoctyes was also analyzed. Confocal images of the intracellular localization of PA-nanospheres were captured by LSCM and processed using ImageJ. Analysis of the images provided the date shown in Table 8-1.

TABLE 8-1

Internalization of Polyanhydride Nanoparticles.

| Polymer | Percent monocytes with internalized nanoparticles: 2 h (phagocytosis) | Percent monocytes with internalized nanoparticles: 48 h (phagocytosis and endocytosis) |
|---|---|---|
| Poly(SA) | 88% ± 17% | 96% ± 11% |
| 20:80 CPH:SA | 27% ± 15% | 91% ± 22% |
| 50:50 CPH:SA | 8% ± 11% | 53% ± 28% |

The polyanhydride particles show significant sustained release properties and are more effective at killing microbes for extended periods of time with a fraction of an equivalent does of a solubilized antibiotic.

Example 9

Polyanhydride Nanospheres Provide Enhanced Killing of Microbes

Antibiotics encapsulated in the polyanhydride nanospheres described herein demonstrate significantly effective killing of *Mycobacterium avium* paratuberculosis compared to solubilized antibiotics alone. Examples of the antibiotics tested include amikacin and rifampicin. Other active agents, such as those described herein, can be encapsulated in the polyanhydride nanospheres to kill microbes in an extracelluar fashion, either in vivo or in vitro, such as in broth and infected macrophage cultures. FIGS. 15-21 and Table 9-1 illustrate data obtained from experiments demonstrating the effectiveness of these compositions.

FIG. 15 illustrates viability of *Mycobacterium avium* subsp. *paratuberculosis* (MAP) at 24 hours and 48 hours after treatment with PBS solubilized amikacin or polyanhydride particles containing 10 μg/mL amikacin. The experiments were carried out with amikacin (16 μg/mL), followed by reduction by 1 log. The antibiotic resistance was measured at days 4 and 7. See Pelligrin (*J. Antimicrobial Chemotherapy,* 2006) for assessing antimicrobial activity of amikacin on MAP in broth culture.

In the assay used to provide the results illustrated in FIG. 15, the soluble 10 μg/mL (lower dose) was measured by % live MAP. Direct comparison of standard soluble amikacin added to MAP cultures showed minimal antimicrobial activity. In contrast, amikacin loaded into 20:80 CPH:SA nanospheres killed>50% of MAP by 48 hours. Also, amikacin loaded into 20:80 CPTEG:CPH exhibited>20% killing of MAP. This interaction with the bacteria was anhydride polymer chemistry dependent as evident by no antimicrobial activity being detected in cultures treated with amikacin loaded 50:50 CPTEG:CPH nanoparticles.

FIGS. 16 and 17 show data from the results of experiments carried out with the following treatment groups:

5% amikaycin (Sigma);

1 20:80 CPH:SA (5% amikaycin);

2 20:80 CPTEG:CPH (5% amikaycin); and

3 50:50 CPTEG:CPH (5% amikaycin).

The data is summarized in Table 9-1.

TABLE 9-1

| Broth Time | Sample | 1.25 μg/mL | 10 μg/mL |
|---|---|---|---|
| 24 hrs | untreated | 94.23% | 93.01% |
| | Soluble | 93.79% | 90.08% |
| #1 | 20:80 CPH:SA | 82.14% | 59.74% |
| #2 | 20:80 CPTEG:CPH | 86.91% | 78.95% |
| #3 | 50:50 CPTEG:CPH | 92.80% | 90.34% |
| 48 hrs | untreated | 88.91% | 94.44% |
| | Soluble | 88.42% | 84.75% |
| #1 | 20:80 CPH:SA | 81.68% | 43.72% |
| #2 | 20:80 CPTEG:CPH | 83.40% | 69.16% |
| #3 | 50:50 CPTEG:CPH | 85.93% | 82.44% |

FIG. 16 illustrates viability of MAP in broth at 24 hours and 48 hours after treatment with PBS solubilized amikacin or polyanhydride particles containing 1.25 μg/mL amikacin. FIG. 17 illustrates viability of MAP in broth at 24 hours and 48 hours after treatment with PBS solubilized amikacin or polyanhydride particles containing 10 μg/mL amikacin.

Determinations of intracellular bacterial viability and extracellular bacterial killing for this Example were determined as schematically illustrated in FIG. 18. Metabolically active MAP are FITC positive. Fluorescence intensity for individual bacteria is recorded by flow and gated against cultures with lysed cells without bacteria. Forward and side scatter was consistent with intact MAP. The % live MAP was measured for each sample and two biological replicates were carried out for each sample.

FIG. 19 illustrates percent viability of intracellular MAP in U937 human pro-monocytes at 24 hours (left bars) and 48 hours (right bars) after treatment with PBS solubilized amikacin or polyanhydride particles containing 10 μg/mL amikacin. The 20:80 CPTEG:CPH formulation used in these experiments had significantly higher killing of intracellular MAP than soluble amikacin.

FIG. 20 illustrates percent cell viability of intracellular MAP in RAW264 at 24 hours and 48 hours after treatment with PBS solubilized amikacin or polyanhydride particles containing 10 μg/mL amikacin. Thus, 50:50 CPTEG:CPH particles containing an active agent is surprisingly effected at killing extracellular microbes.

FIG. 21 illustrates percent viability of intracellular MAP in J774A at 24 hours and 48 hours after treatment with PBS solubilized amikacin or polyanhydride particles containing 10 μg/mL amikacin. Encapsulation of the amikacin antibiotic into 20:80 CPTEG:CPH nanoparticle formulation enabled significantly higher antimicrobial activity than the equivalent dose of soluble antibiotic. Moreover, given that antibiotic release is delayed, this higher degree of killing occurs with an effectively lower concentration of available (released) antibiotic. Exact antibiotic concentration released can be quantified by HPLC.

Accordingly, Applicants have demonstrated that particle encapsulation using polyanhydride copolymers enables higher antimicrobial activity against microbes such as *Escherichia coli, Yersinia, Brucella* and *Mycobacterium*.

Encapsulated antibiotics were released from eroding nanoparticles in a controlled manner, evidenced by continual antimicrobial activity using filter disk passage experiments. Optimal copolymer formulations vary depending on the particular microbe targeted and whether the treatment is to be given in vitro or in vivo. Several antibiotics have been successfully encapsulated using variable copolymer formulations, and it is believed that virtually any sort of cargo can be encapsulated in the polyanhydride particles, including proteins and bacterial lysates.

Example 10

Pharmaceutical Dosage Forms

The following formulations illustrate representative pharmaceutical dosage forms that may be used for the therapeutic or prophylactic administration of a PANS composition described herein (hereinafter referred to as 'Composition X'):

| (i) Tablet 1 | mg/tablet |
|---|---|
| 'Composition X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Composition X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Composition X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection 1 (1 mg/mL) | mg/mL |
|---|---|
| 'Composition X' | 1.0 |
| Dibasic sodium phosphate | 12.0 |
| Monobasic sodium phosphate | 0.7 |
| Sodium chloride | 4.5 |
| 1.0N Sodium hydroxide solution (pH adjustment to 7.0-7.5) | q.s. |
| Water for injection | q.s. ad 1 mL |

| (v) Injection 2 (10 mg/mL) | mg/mL |
|---|---|
| 'Composition X' | 10.0 |
| Monobasic sodium phosphate | 0.3 |
| Dibasic sodium phosphate | 1.1 |
| Polyethylene glycol 400 | 200.0 |
| 01N Sodium hydroxide solution (pH adjustment to 7.0-7.5) | q.s. |
| Water for injection | q.s. ad 1 mL |

| (vi) Aerosol | mg/can |
|---|---|
| 'Composition X' | 20 |
| Oleic acid | 10 |
| Trichloromonofluoromethane | 5,000 |
| Dichlorodifluoromethane | 10,000 |
| Dichlorotetrafluoroethane | 5,000 |

These formulations may be prepared by conventional procedures well known in the pharmaceutical art. It will be appreciated that the above pharmaceutical compositions may be varied according to well-known pharmaceutical techniques to accommodate differing amounts and types of active ingredient 'Composition X'. Aerosol formulation (vi) may be used in conjunction with a standard, metered dose aerosol dispenser. Additionally, the specific ingredients and proportions are for illustrative purposes. Ingredients may be exchanged for suitable equivalents and proportions may be varied, according to the desired properties of the dosage form of interest.

While specific embodiments have been described above with reference to the disclosed embodiments and examples, these embodiments and examples are only illustrative and do not limit the scope of the invention. Changes and modifications can be made in accordance with ordinary skill in the art without departing from the invention in its broader aspects as defined in the following claims.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A polyanhydride nanoparticle comprising:
   polyanhydride polymers in the form of a nanoparticle, wherein the
   nanoparticle is substantially spherical in shape and has an average diameter of about 100 nm to about 900 nm; and
   an antimicrobial agent located in the interior of the nanoparticle;
   wherein the polyanhydride polymers comprise anhydride copolymers of 1,8-bis(carboxyphenoxy)-3,6-dioxaoctane (CPTEG) and 1,ω-bis(carboxyphenoxy)($C_2$-$C_{10}$)alkane units,
   and wherein the ratio of 1,8-bis(carboxyphenoxy)-3,6-dioxaoctane (CPTEG) to 1,ω-bis(carboxyphenoxy)($C_2$-$C_{10}$)alkane in the nanoparticle is about 20:80 to about 50:50.

2. The polyanhydride nanoparticle of claim 1 wherein the 1,ω-bis(carboxy-phenoxy)($C_2$-$C_{10}$)alkane comprises 1,6-bis-(p-carboxyphenoxy)hexane (CPH) anhydrides.

3. The polyanhydride nanoparticle of claim 1 wherein the 1,ω-bis(carboxy-phenoxy)($C_2$-$C_{10}$)alkane is a 1,ω-bis(carboxy-phenoxy)($C_4$-$C_8$)alkane.

4. The polyanhydride nanoparticle of claim 1 wherein the antimicrobial agent comprises doxycycline.

5. The polyanhydride nanoparticle of claim 4 wherein the nanoparticle further comprises a second antimicrobial agent.

6. The polyanhydride nanoparticle of claim 1 wherein the antimicrobial agent is selected from the group consisting of amikacin, cephalexin, cephalosporin, ciprofloxacin, doxycycline, erythromycin, ethambutol, gentamicin, isoniazid, penicillin, rifampin, spectinomycin, streptomycin, sulfa, tetracycline, trimethoprim-sulfamethoxazole, vancomycin, or a combination thereof.

7. The polyanhydride nanoparticle of claim 1 wherein the polyanhydride nanoparticle encapsulates an average of about 1 μg/mL to about 12 μg/mL of the antimicrobial agent.

8. The polyanhydride nanoparticle of claim 5 wherein the second antimicrobial agent is bacillomycin or a heavy metal.

9. A method to kill microbes or inhibit the growth of microbes comprising:
contacting microbes with an effective antimicrobial amount of a composition that includes polyanhydride nanoparticles of claim 1;
wherein the nanoparticles degrade by surface erosion in the presence of the microbes over a period of time to release the antimicrobial agents from the interior of the nanoparticles, thereby killing the microbes or inhibiting the growth of the microbes.

10. A method to treat a microbial infection in an animal comprising:
administering to an animal in need of such treatment an effective antimicrobial amount of a composition that includes polyanhydride nanoparticles of claim 1;
wherein the nanoparticles accumulate in infected monocytes, dendritic cells, or both, and the nanoparticles degrade by surface erosion over a period of time to release the antimicrobial agents so as to contact and kill microbes or inhibit the growth of microbes causing the infection, thereby treating the microbial infection.

11. The method of claim 10 wherein the microbial infection is an infection that causes a chronic disease.

12. The method of claim 11 wherein the microbial infection is a bacterial infection.

13. The method of claim 12 wherein the bacterial infection is caused by a bacterium selected from the group consisting of *Bordetella*, *Borrelia*, *Brucella*, *Burkholderia*, *Chlamydia*, *Erhlichia*, *Francisella*, *Mycobacterium*, *Rickettsia*, *Salmonella*, or *Yersinia*.

14. The method of claim 12 wherein the microbial infection causes a disease selected from the group consisting of Bacterial meningitis, Brucellosis, Erhlichiosis, Glanders, Johne's, mastitis, Legionella, Lyme disease, Mycobacteria disease complex, Mycoplasmosis, Q-fever, Salmonellosis, Shigellosis, or Tuberculosis.

15. The method of claim 10 wherein the antimicrobial agent is doxycycline.

16. The method of claim 15 wherein the polyanhydride nanoparticles encapsulate an average of about 1 μg to about 12 μg of the antimicrobial agent per particle.

17. The method of claim 16 wherein the polyanhydride nanoparticles further comprise an additional antimicrobial agent.

18. The method of claim 17 wherein the additional antimicrobial agent is a heavy metal.

19. A method to treat a microbial infection in an animal comprising:
administering to an animal in need of such treatment an effective antimicrobial amount of a composition that includes polyanhydride nanoparticles that encapsulate a plurality of antimicrobial agents;
wherein the polyanhydride nanoparticles comprise copolymers of (a) 1,8-bis(carboxyphenoxy)-3,6-dioxaoctane (CPTEG) anhydrides, and (b) 1,6-bis(p-carboxyphenoxy)hexane (CPH) anhydride in a ratio of about 20:80 to about 50:50;
wherein the nanoparticles are substantially spherical in shape and have an average diameter of about 100 nm to about 900 nm; and
wherein the nanoparticles accumulate in infected monocytes, dendritic cells, or both, and degrade by surface erosion over a period of time to release the antimicrobial agents into the infected monocytes or dendritic cells; thereby treating the microbial infection.

20. A method to deliver antimicrobial agents to cells infected with microbes comprising:
contacting cells infected by microbes with an effective amount of a composition that includes polyanhydride nanoparticles;
wherein the polyanhydride nanoparticles comprise copolymers of (a) 1,8-bis(carboxyphenoxy)-3,6-dioxaoctane (CPTEG) anhydrides, and (b) 1,6-bis(p-carboxyphenoxy)hexane (CPH) anhydride in a ratio of about 20:80 to about 50:50;
wherein the nanoparticles are substantially spherical in shape and have an average diameter of about 100 nm to about 900 nm;
the copolymers of the polyanhydride particles form a matrix around a plurality of antimicrobial agents within the particles; and
the nanoparticles accumulate in the cells infected by microbes, and degrade by surface erosion over a period of time to release the antimicrobial agents, thereby delivering the antimicrobial agents to the microbes.

* * * * *